(12) United States Patent
Kawa et al.

(10) Patent No.: US 7,993,687 B2
(45) Date of Patent: Aug. 9, 2011

(54) COMPOSITIONS AND METHODS FOR MANAGEMENT OF DIABETES

(76) Inventors: Julianne Marie Kawa, Winnipeg (CA); Carla Gwen Taylor, Winnipeg (CA); Peter Charles Zahradka, Winnipeg (CA)

( * ) Notice: Subject to any disclaimer, the term of this patent is extended or adjusted under 35 U.S.C. 154(b) by 49 days.

(21) Appl. No.: 11/484,557

(22) Filed: Jul. 12, 2006

(65) Prior Publication Data

US 2008/0014294 A1    Jan. 17, 2008

(51) Int. Cl.
*A61K 36/00* (2006.01)
(52) U.S. Cl. ......................... 424/776; 424/725
(58) Field of Classification Search .................. None
See application file for complete search history.

(56) References Cited

U.S. PATENT DOCUMENTS

| | | | |
|---|---|---|---|
| 6,048,842 A | 4/2000 | Tsujihara et al. | |
| 6,096,364 A * | 8/2000 | Bok et al. | 426/590 |
| 6,162,795 A * | 12/2000 | Obendorf et al. | 514/35 |
| 6,451,353 B1 * | 9/2002 | Pei et al. | 424/725 |
| 6,800,433 B1 * | 10/2004 | Honda et al. | 435/4 |
| 6,825,173 B2 * | 11/2004 | Obendorf et al. | 514/35 |
| 7,011,856 B2 * | 3/2006 | Kosuna | 424/750 |
| 2005/0158412 A1 | 7/2005 | Su et al. | |
| 2005/0204619 A1 * | 9/2005 | Park et al. | 47/58.1 R |
| 2006/0029690 A1 * | 2/2006 | Kwong et al. | 424/776 |

FOREIGN PATENT DOCUMENTS

| | | |
|---|---|---|
| WO | WO 98/50049 A1 | 11/1998 |
| WO | WO 01/89532 A1 | 11/2001 |
| WO | WO 2005/063226 A1 | 7/2005 |
| WO | WO 2005/067489 A2 | 7/2005 |

OTHER PUBLICATIONS

Julianne M. Kawa, Carla G. Taylor, and Roman Przybylski (2003) Buckwheat Concentrate Reduces Serum Glucose in Streptozotocin-Diabetic Rats. J. Agric. Food Chem. 51: 7287-729.

* cited by examiner

*Primary Examiner* — Christopher R. Tate
(74) *Attorney, Agent, or Firm* — Gowling Lafleur Henderson LLP

(57) ABSTRACT

A buckwheat extract comprising at least myo-inositol, D-chiro-inositol, a fagopyritol, one MAPK-stimulating compound, and one glucose-uptake inhibiting compound. A substantially pure glucose-uptake inhibiting compound selected from a buckwheat extract. A method for providing a glucose-uptake inhibiting extract from buckwheat seed comprising first contacting said buckwheat seed with a non-polar solvent, then contacting said buckwheat seed with a polar aprotic solvent, and then finally contacting said buckwheat seed with a third solvent. The third solvent may be a polar aprotic solvent or a polar protic solvent. The extract produced by contacting buckwheat seed with the third solvent is dried to remove the solvent therefrom. Compositions comprising dried glucose-uptake inhibiting buckwheat extracts and purified compounds therefrom.

21 Claims, 21 Drawing Sheets

Fig. 2
(i) Control rats in fed state
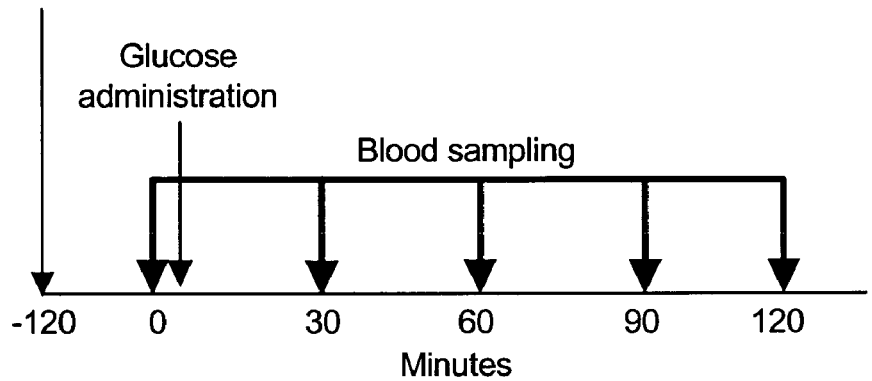
(ii) STZ-diabetic rats in fed state
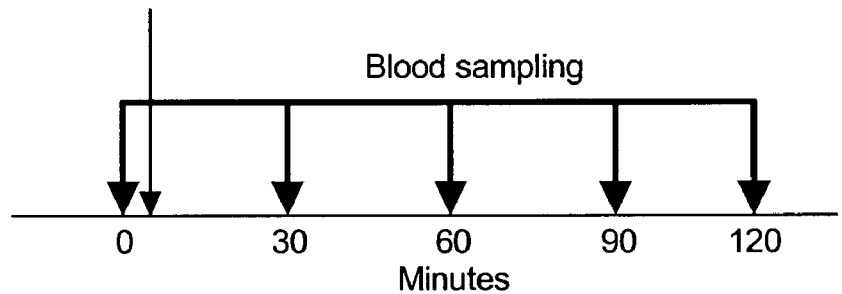
(iii) STZ-diabetic rats fasted for 4 hrs
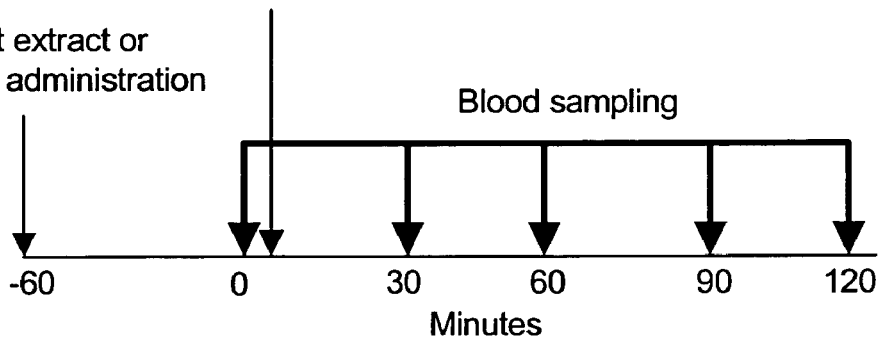

Fig. 16
(i)
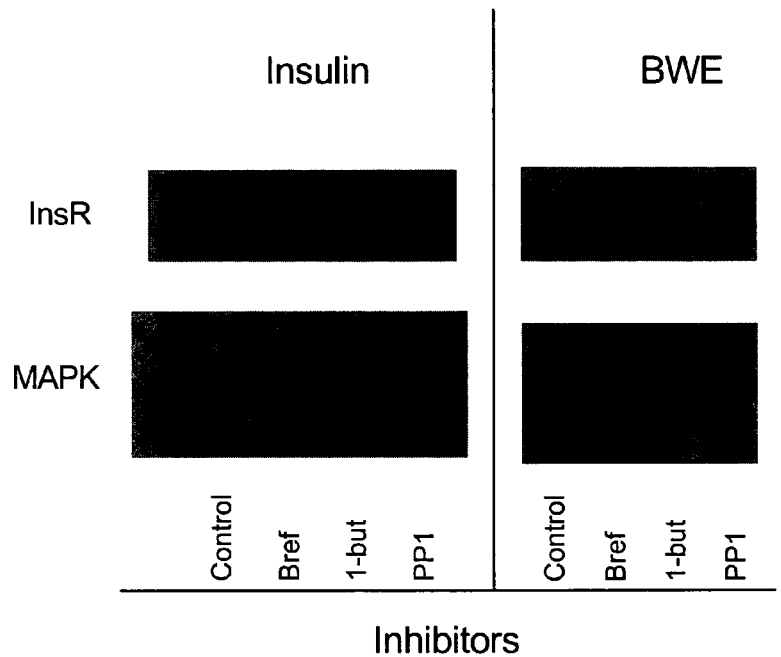
(ii) 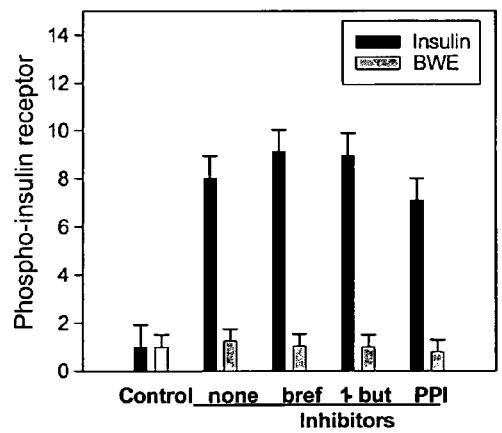
(iii) 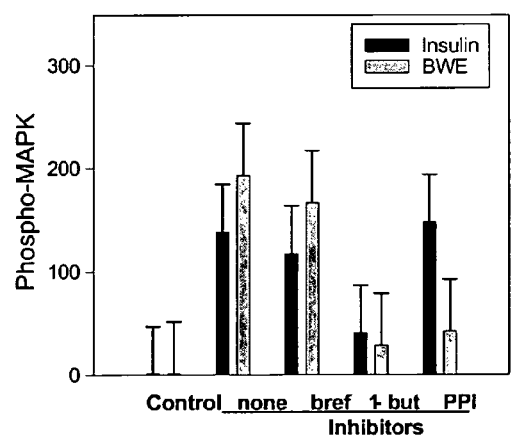

Fig. 17
(i) p70$^{S6K}$ (Thr$^{421}$)
Ctrl     Ins     BWE
(ii) p70$^{S6K}$ (Thr$^{389}$)
Ctrl     Ins     BWE
(iii) S6
Ctrl     Ins     BWE Fig. 18
(i)
p70$^{S6K}$(Thr$^{421}$)
CTRL     BWE     BWE+PD     BWE+LY
(ii)
p70$^{S6K}$(Thr$^{421}$)
CTRL     INS     INS+PD     INS+LY
(iii)
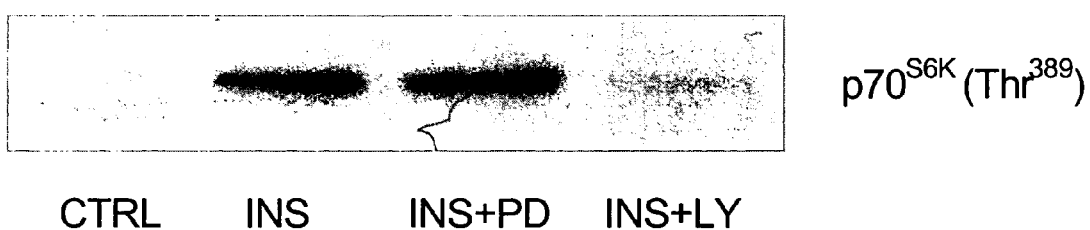
p70$^{S6K}$(Thr$^{389}$)
CTRL     INS     INS+PD     INS+LY

COMPOSITIONS AND METHODS FOR MANAGEMENT OF DIABETES

FIELD OF THE INVENTION

This invention relates to compositions and methods for the management of Type 1 and Type 2 diabetes.

BACKGROUND OF THE INVENTION

Insulin is a mammalian hormone essential for the utilization of glucose derived from food intake, from the blood system by the liver, muscle and adipose tissue. Insulin affects glucose, protein and lipid metabolism by binding to its receptor, which subsequently activates various cell signal transduction pathways that mediate the biological actions of insulin. Among the downstream effects of insulin binding is regulation of the glucose transporter GLUT4 that results in increased glucose uptake in skeletal muscle and adipose. Insulin also increases glucose utilization by affecting key enzymes involved in glucose metabolic pathways primarily at the level of transcription, and insulin increases glucose storage by activating signal transduction proteins in pathways leading to glycogen synthesis. Insulin maintains glucose homeostasis and reduces hyperglycemia by decreasing hepatic glucose production and release, and increasing glucose uptake, utilization, and storage in body tissues. Insulin directly affects glucose uptake in skeletal muscle and adipose tissue through its regulation of the GLUT4 glucose transporter. The liver is one of the major targets of insulin for glucose uptake, utilization, and storage, but insulin's effects on hepatic glucose uptake are different than in muscle and adipose. In response to insulin, hepatic glucose uptake is dramatically augmented due to increased activity of enzymes involved in glucose utilization and storage via pathways of glycolysis and glycogenesis. This leads to a decrease in the intracellular glucose concentration, and consequently, glucose enters hepatocytes via facilitated diffusion in response to the concentration gradient that forms. In contrast to GLUT4 in skeletal muscle and adipose, the hepatic glucose transporter (GLUT2) is insulin independent. Other downstream effects of insulin receptor activation include increased lipogenesis and increased protein synthesis.

Type 1 diabetes mellitus (DM) occurs when the body does not make enough or alternatively, does not make any insulin, thereby causing blood sugar levels to increase significantly after food intake, resulting in a condition known as hyperglycaemia. Extended periods of hyperglycaemia can result in excessive oxidation of fatty acids resulting in production of ketones which acidify the blood giving rise to a condition known as ketosis. Type 1 DM can be treated by insulin injections at dosage levels calculated to maintain blood sugar levels within a target range. However, if the insulin injections are not correctly balanced with food intake and exercise, blood sugar levels can fall to hypoglycaemic levels which if untreated, can result in coma and death.

Type 2 DM occurs when the body isn't able to properly metabolize the insulin it produces. Depending on the severity, Type 2 DM can be managed by: (1) diet and exercise, (2) oral intake of insulin or insulin mimetics, or (3) insulin injections. Mechanisms of action for the oral agents include stimulation of pancreatic insulin secretion (e.g., sulfonylurea compounds), inhibition of hepatic glucose production (e.g., metformin), enhancement of peripheral insulin sensitivity (e.g., thazolidinediones), and slowing the rate of carbohydrate absorption (e.g., α-glucosidase inhibitors). Each of the Type 2 DM therapies must be carefully managed to avoid incidences of hypoglycaemia and hyperglycaemia.

In the developed world, the prevalence of both types of DM continues to increase, as do the costs of providing treatment to DM sufferers. As a consequence, considerable research efforts have been and continue to focus on increasing the understanding of insulin activity in order to enable development of new DM management strategies, therapies and pharmaceuticals. Among recent developments is the identification and partial characterization of two separate inositol phosphoglycan molecules. In response to insulin, inositol phosphoglycan molecules are hydrolyzed from glycosylphosphatidylinositols that are found in cell membranes. Inositol phosphoglycan molecules are considered putative insulin mediators based on their ability to mimic a large number of the metabolic actions of insulin both in vitro and in vivo. Although the structures of the inositol phosphoglycan molecules have not yet been completely elucidated, one molecule contains myo-inositol and glucosamine, and the other contains D-chiro-inositol and galactosamine as core components. Inositol is a hexahydroxycyclohexane that is structurally related to glucose. There are nine isomers of inositol that differ in their position of hydroxyl groups. Myo-inositol is the most common occurring isomer in plants and animals whereas D-chiro-inositol is relatively rare. In addition to these core components, both types of inositol phosphoglycan molecules also contain neutral sugars and phosphate residues. The origin of the myo-inositol-containing inositol phosphoglycan molecules is thought to be myo-inositol-containing glycosylphosphatidylinositol, as both phospholipase C- and phospholipase D-mediated hydrolysis of glycosylphosphatidylinositol yield biologically active inositol phosphoglycan molecules.

The insulin-like activities of isolated inositol phosphoglycan molecules and their chemically synthesized analogues have been widely investigated and have been previously reviewed (M. Field, 1997, Glycobiology 7: 161-168; D. R. Jones and I. Varela-Nieto, 1998, Cell Biology 30:313-326). It is known that the myo-inositol-containing inositol phosphoglycan molecule stimulates lipogenesis, glucose transport, glycogen synthesis, amino acid transport, protein synthesis, and GLUT-4 translocation in in vitro model systems. It is also known that myo-inositol-containing glycosylphosphatidylinositol molecule stimulates P13K, MAPK activity, but inhibits GSK-3 activity. The MI-IPG is also able to regulate expression of PEPCK in rat hepatocytes.

The D-chiro-inositol-containing inositol phosphoglycan molecule has also demonstrated in vitro insulin mimetic effects including the activation of key protein phosphatases in pathways known to be stimulated by insulin. In particular, it has been demonstrated that the D-chiro-inositol-containing inositol phosphoglycan molecule activates pyruvate dehydrogenase phosphatase and glycogen synthase phosphatase. These enzymes play a key role in the regulation of glucose disposal by oxidative metabolism (glycolysis) and by the non-oxidative route of storage by glycogen synthesis, respectively.

The insulin-mimetic effects of both inositol phosphoglycan molecules have also been demonstrated in vivo. Both inositol phosphoglycan subtypes increased glucose incorporation into diaphragm glycogen in normal rats and reduced hyperglycemia in streptozotocin-induced (STZ) diabetic rats (L. C. Huang, M. C. Fonteles, D. Houston, C. Zhang, and J. Lamer, 1993, Endocrinology 132: 652-657). Prolonged infusion with D-chiro-inositol-containing inositol phosphoglycan molecule normalizes plasma glucose levels in STZ-induced diabetic rats to the same extent observed with insulin but without inducing hypoglycemia (M. Fonteles, M. Almeida, and J. Lamer, 2000, Hormone and Metabolic Research 32: 129-132).

There remains a continuing need to develop new methods and pharmaceuticals suitable for the treatment of DM. In particular, there is a need to identify and characterize new therapeutics that cause a reduction in blood glucose levels, particularly those that are simpler to produce and less expensive than recombinant or naturally sourced insulin derivates. It is well known that the seeds of buckwheat (*Fagopyrum cymosum* (Trev.) Meisn.) contain significant amounts of myo-inositol, D-Chiro-inositol, and galactosyl derivatives of D-Chiro-inositol isomers commonly referred to as "fagopyritols" (Horbowicz and Obendorf, 1994). Analyses of the soluble carbohydrate composition of buckwheat seeds demonstrated the presence of significant levels of at least two galactosyl chiro-inositol isomers commonly known as Fagopyritol A1 and Fagopyritol B1, at least two di-galactosyl chiro-inositol isomers commonly known as Fagopyritol A2 and Fagopyritol B2, and small quantities of a tri-galactosyl chiro-inositol isomer commonly known as Fagopyritol B3. It is also known that the soluble carbohydrate content of buckwheat seed includes about 40% sucrose and 40% Fagopyritol B 1. Furthermore, the fagopyritols are found primarily in the embryo portion of buckwheat groats.

U.S. Pat. No. 6,162,795 and related U.S. Pat. No. 6,492,341 disclose an isolated Fagopyritol A1, an isolated Fagopyritol A2, an isolated Fagopyritol B3, and methods for preparing substantially pure Fagopyritol A1, Fagopyritol A2, Fagopyritol B 1, Fagopyritol B2, Fagopyritol B3 from buckwheat. The methods comprise a first step of preparing a flour from buckwheat seed or seed components, followed by a second step of extracting fagopyritols from the flour using an alcohol or an alcohol/water solvent. It is noted that '795 defines "fagopyritol" being substantially free of other naturally occurring buckwheat components.

U.S. Patent Application Pub. No. 2006/0029690 discloses methods for extracting tartary buckwheat with 30% ethanol to provide a biologically active component for treatment of hypoglycaemia.

U.S. Pat. No. 6,451,353 discloses the extraction from buckwheat rhizomes, of compositions useful for treating cancers and/or respiratory tract ailments. The compositions provided are tannins and/or procyanidins.

SUMMARY OF THE INVENTION

The exemplary embodiments of the present invention, at least in preferred forms, are directed to extracts from buckwheat (i.e., *Fagopyrum esculentum*) seed for managing serum glucose levels in an individual.

According to a preferred embodiment, there is provided a buckwheat extract configured for managing serum glucose levels in an individual. The buckwheat extract comprises myo-inositol, D-chiro-inositol, at least one naturally occurring MAPK-stimulating compound, and at least one naturally occurring glucose-uptake inhibiting compound. In a preferred form, the at least one glucose-uptake inhibiting compound is an inhibitor of a sodium-dependent glucose transporter.

According to another preferred embodiment, there is provided a method for producing an extract from buckwheat seed. The method comprises a three-step process wherein the first step comprises contacting the buckwheat seed with a non-polar solvent to produce a first extract, then contacting the buckwheat seed a second time with a polar aprotic solvent to produce a second extract, and then again contacting the buckwheat seed a third time with a polar protic solvent to produce a third extract. Alternatively, the buckwheat seed may be contacted a third time with a polar aprotic solvent to produce the third extract.

According to one aspect, the buckwheat seed is fractionated into seed portions prior contacting with the first solvent. In a preferred form, buckwheat seed portions contacted with the first solvent are groats, bran, "shorts" comprising testa, cotyledon, and embryo with some endosperm, and mixtures thereof. It is preferred that the buckwheat seed portions are ground into a fine powder prior to contacting with the first solvent.

According to another aspect, the buckwheat seed are ground into a flour prior to contacting with first solvent.

According to a yet another aspect, the first solvent i.e., a non-polar solvent is selected from the group consisting of hexane, benzene, toluene, diethyl ether, chloroform, ethyl acetate, and dichloromethane. In a preferred form, the first solvent is chloroform.

According to a further aspect, the second solvent, i.e., a polar aprotic solvent is selected from the group consisting of 1,4-dioxane, tetrahydofuran, acetone, acetonitrile, dimethylformamide, and dimethyl sulfoxide. It is preferred that the second solvent is tetrahydrofuran.

According to a yet further aspect, the third solvent is selected from a group consisting of polar aprotic solvents (e.g., 1,4-dioxane, tetrahydofuran, acetone, acetonitrile, dimethylformamide, and dimethyl sulfoxide) and polar protic solvent (e.g., ispropanol, n-propanol, ethanol, methanol, and water). In a preferred form, the third solvent is acetone. In another preferred form, the third solvent is methanol.

According to another aspect, said third buckwheat extract is provided for managing serum glucose levels in an individual wherein the extract comprises at least one substantially pure naturally occurring glucose-uptake inhibiting compound. In a preferred form, the at least one glucose-uptake inhibiting compound is an inhibitor of a sodium-dependent glucose transporter.

According to yet another preferred embodiment of the present invention, there are provided compositions comprising buckwheat extracts configured as disclosed herein for managing serum glucose levels in an individual.

According to one aspect, there is provided a nutraceutical composition comprising a nutraceutical carrier and a buckwheat extract comprising at least one naturally occurring compound for inhibiting systemic glucose uptake into an individual's bloodstream. In a preferred form, the at least one naturally occurring compound is a sodium-dependent glucose transporter inhibitor.

According to another aspect, there is provided a functional food composition comprising a functional food carrier and a buckwheat extract comprising at least one naturally occurring compound for inhibiting systemic glucose uptake into an individual's bloodstream. In a preferred form, the at least one naturally occurring compound is a sodium-dependent glucose transporter inhibitor.

According to yet another aspect, there is provided a pharmaceutical composition comprising a pharmaceutical carrier and a naturally occurring compound useful for inhibiting systemic glucose uptake into an individual's bloodstream, said naturally occurring compound extracted from buckwheat seed. In a preferred form, the naturally occurring compound is a sodium-dependent glucose transporter inhibitor.

BRIEF DESCRIPTION OF THE DRAWINGS

The present invention will be described in conjunction with reference to the following drawings, in which:

FIG. 2 illustrates the experimental designs used for (i) intraperitoneal glucose tolerance test 2 hours following an acute dose of a buckwheat extract (BWE) or a placebo given to normal rats, (ii) fed-state response to an acute dose of BWE or a placebo in STZ rats, and (iii) oral glucose tolerance test 1 hour following an acute dose of BWE or a placebo given to fasted STZ rats;

FIG. 16 shows the effects of inhibition of phospholipase D (butanol sensitive), Src kinase (PP-1 sensitive), and Arf3 (brefeldin sensitive) on BWE and insulin stimulated phosphorylation of insulin receptor (InsR) and mitogen-activated protein kinase (MAPK) assessed by Western blot analysis. Following a 15 minute preincubation with the indicated inhibitors, H4IIE cells were treated with either insulin or the BWE for 6 minutes. Each experiment was replicated three times. Band intensities on each blot were quantified by scanning densitometry and plotted as means ±SE (n=3). The effects of inhibitors on BWE and insulin-stimulated phosphorylation of B) InsR and C) MAPK are shown. An * indicates statistical significance (p<0.05) for insulin±inhibitors versus the control and # indicates statistical significance (p<0.05) for BWE±inhibitors versus the control;

FIG. 17 shows the effects of insulin (INS) and BWE on phosphorylation of (i) $p70^{S6K}(Thr^{421})$, (ii) $p70^{S6K}(Thr^{389})$ and (iii) ribosomal protein S6 assessed by Western blot analysis. H4IIE cells were treated with each agent individually for 6 minutes, with untreated cells serving as the control (CTRL);

FIG. 18 shows the effects inhibition of MAPK (PD98059 (PD)-sensitive) and PI3K (LY294002 (LY)-sensitive) on (i) buckwheat concentrate (BWE)-stimulated phosphorylation of $p70^{S6K}$ ($Thr^{421}$), (ii) insulin (INS)-stimulated phosphorylation of $p70^{S6K}$ ($Thr^{421}$) and (iii) INS-stimulated phosphorylation of $p70^{S6K}$ ($Thr^{189}$). Following a 15-minute pre-incubation with the indicated inhibitors, H4IIE cells were treated with either INS or the BWE for 6 minutes, with untreated cells serving as the control (CTRL);

DETAILED DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, invention, the preferred methods and materials are now described.

As used herein, "buckwheat" refers to the seed harvested from *Fagopyrum cymosum* (Trev.) Meisn.

As used herein, "groats" are the hulled and crushed seeds of buckwheat.

As used herein, "hull" refers to hard protective outer covering of a seed, i.e., the seed coat.

As used herein, "de-hulled" refers to a seed which has had its hard protective outer covering of a seed, i.e., the seed coat, removed.

As used herein, "bran" refers to outer layer of cereal grains comprising the aleurone and pericarp.

As used herein, "fagopyritol" is a general term used to refer to an unspecified α-galactosyl D-chiro-inositol or its salt or its derivative, substantially free of other naturally occurring buckwheat components.

As used herein, "effective amount" refers to the administration of an amount of a given compound that achieves a desired effect.

As used herein, "purified" does not require absolute purity but is instead intended as a relative definition. For example, purification of a starting material or a natural material to at least one order of magnitude, preferably two or three orders of magnitude is expressly contemplated as falling within the definition of "purified".

As used herein, the term, "isolated" requires that the material be removed from its original environment.

As used herein, the term "treating" in its various grammatical forms refers to preventing, curing, reversing, attenuating, alleviating, minimizing, suppressing or halting the deleterious effects of a disease state, disease progression, disease causative agent or other abnormal condition.

Figure 1:
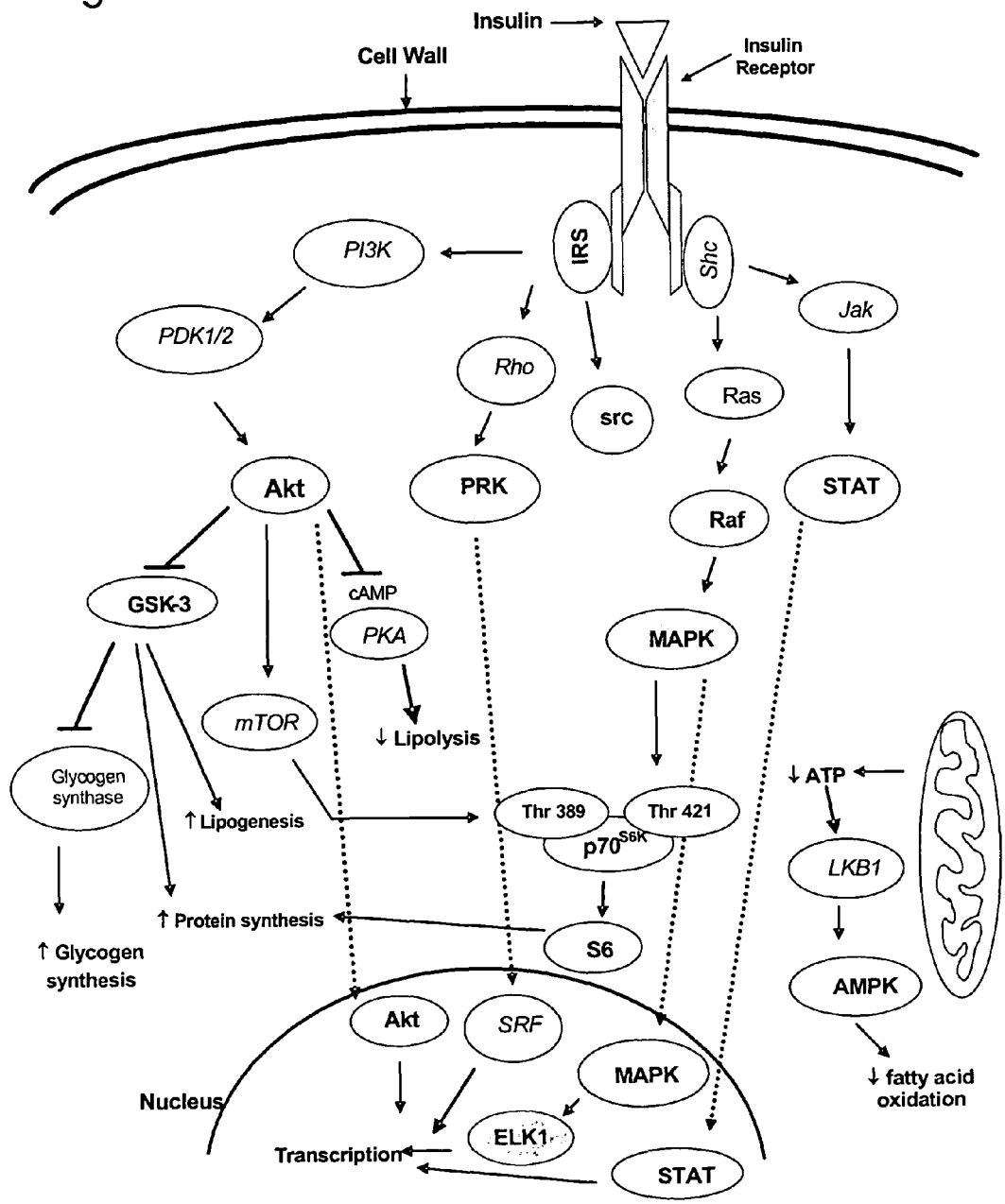
FIG. 1 is a schematic flowchart of the cell signal transduction pathways activated by insulin. Signal transduction proteins in boldface within grey circles were tested for stimulation by the buckwheat concentrate.

As used herein, the following acronyms refer to the term adjacent each acronym:
AMPK AMP-activated protein kinase
APS ammonium persulfate
ATP adenosine triphosphate
BSA bovine serum albumin
BWE buckwheat extract
BW HIGH high dose of buckwheat extract
BW LOW low dose of buckwheat extract
CTRL control
D-CI D-chiro-inositol
DM diabetes mellitus
DM-1 type 1 diabetes mellitus
DM-2 type 2 diabetes mellitus
FBS fetal bovine serum
GIP glucose-dependent insulinotropic polypeptide
GK Goto-Kakizaki
GLUT Na$^+$ independent glucose transporter
GLP-1 glucagon-like peptide-1
GPI glycosylphosphatidylinositol
GCK-3 glycogen synthase kinase-3
HbA1$_c$ glycosylated hemoglobin
HRP horseradish peroxidase IGF/IR insulin-like growth factor/insulin receptor
IGT impaired glucose tolerance
INS insulin
InsR insulin receptor
IPG inositol phosphoglycan
IPGTT intraperitoneal glucose tolerance test
IRS insulin receptor substrate
JAK janus kinase
MAPK mitogen activated protein kinase
MI myo-inositol
mTOR mammalian target of rapamycin
NADH nicotinamide adenine dinucleotide
OGTT oral glucose tolerance test
PDH pyruvate dehydrogenase
PEPCK phosphoenolpyruvate carboxykinase
PKA cAMP-dependent protein kinase A
PLD phospholipase D
PL HIGH placebo high dose
PL LOW placebo low dose
PI3K phosphatidylinositol 3-kinase
P-MAPK phosphorylated mitogen activated protein kinase
PPAR peroxisome proliferator-activated receptor
PRK protein kinase C-related kinase
PSS physiological salt solution
PVDF polyvinylidenedifluoride
SDBW Sprague-Dawley buckwheat
SDC Spague-Dawley control
SDS sodium dodecyl sulfate
Ser serine
SGLT $Na^+$ dependent glucose transporter
SMC-PBS smooth muscle cell phosphate-buffered saline
STAT signal transducers and activators of transcription
STZ streptozotocin
STZ rat streptozotocin-induced diabetic rat
TBST Tris-buffered saline with tween-20
TCA tricarboxylic acid cycle
TEMED N,N,N',N'-Tetramethylethylenediamine
Thr threonine
Tyr tyrosine
TZD thiazolidinediones Insulin activates numerous cell signalling pathways upon binding to its receptor. Among the downstream effects resulting from these pathway are increased glucose uptake, utilization and storage, as well as decreased glucose production and release, increased lipogenesis and protein synthesis. FIG. 1 shows a schematic flowchart of the current understanding based on prior art disclosures (Table 1), of the cell signal transduction pathways activated by insulin. Insulin binding promotes the activation and autophosphorylation of its receptor which then catalyses the phosphorylation of several substrates including IRS. Tyrosine-phosphorylated IRS then activates PI3K which has a major role in insulin function, mainly via the activation of Akt. Activated Akt induces glycogen synthesis through inhibition of glycogen synthase kinase-3 (GSK-3). Promotion of fatty acid synthesis and inhibition of lipolysis are also downstream of activated Akt. Protein synthesis is also downstream from $p70^{S6K}$ which phosphorylates ribosomal protein S6. The Ras/MAPK and Akt/mTOR pathways both participate in this pathway by mediating the phosphorylation of distinct Thr residues on $p70^{S6K}$. Insulin mediates transcription in the cell nucleus through the Janus kinase (JAK)/signal transducers and activators of transcription (STAT) pathway, the Akt cascade, as well as by activation of the Ras/mitogen activated protein kinase (MAPK) pathway. Various enzymes involved in glucose metabolism are also regulated by insulin's effect on gene transcription. Modification of MAPK results in its activation and subsequent translocation into the riucleus, where it mediates the phosphorylation of specific transcription factors. Hepatic glucokinase is an enzyme that converts glucose to a form that is both trapped in the cell and capable of being further metabolized. Insulin increases expression of this enzyme as well as other enzymes and proteins involved in glucose metabolism.

Insulin mimetic compounds can also stimulate phosphorylation of proteins within the pathways shown in FIG. 1, thus inducing similar biological effects. Based on the prior art disclosures regarding preparation and functional assessments of BWE containing elevated levels of myo-inositol (MI) and D-chiro-inositol, (DCI) those skilled in these arts would have predicted that the insulin-mimetic activities associated with BWE were due to the presence of MI and DCI. We have surprisingly found that BWE affects blood glucose via a different pathway and that BWE provided as disclosed herein, blocks glucose uptake into the bloodstream as opposed to insulin-mediated and/or insulin-mimetic-mediated glucose uptake, utilization and storage. Specifically, it is known to those skilled in these arts that administration of too much insulin to a diabetic individual can result in their blood glucose levels falling significantly below normoglycemia thus resulting in hypoglycemia which can have severe medical consequences for the individual. However, as disclosed herein, the BWE of the present invention and fractions thereof and purified compounds therefrom reduce elevated levels of blood glucose, i.e., hyperglycemia, to normal levels i.e., normoglycemia, thereby providing compositions, compounds and methods-of-use for improved glycemic management and control in diabetic individuals.

The methods for providing the buckwheat extract of the present inventions, fractions thereof and compounds therein and methods for their use are described in more detail in the following examples.

TABLE 1

Inhibitors of signal transduction proteins in the insulin signalling pathway.

| Compound | Inhibits phosphorylation of | Working concentration | Prior art Reference |
| --- | --- | --- | --- |
| PD98059 | MAPK | $10^{-5}$ M | Yau et al., 1999, Eur. J. Biochem. 266: 1147-1157 |
| Brefeldin A | phospholipases | 50 μg/mL | Li et al, 1998, Arch. Oral Biol. 43: 211-219 |
| 1-butanol | PLD1 | 0.3% | Morton et al., Brit. J. Pharmacol. 115: 361-367 |
| PP1 | src | $10^{-5}$ M | Zahradka et al, 2004, Endocrinology 145: 2978-2987 |
| U73122 | PLC | $10^{-5}$ M | Smith et al, 1990, J. Pharmacol. Exp. Therap. 253: 688-697 |
| Raf kinase 1 inhibitor | Raf1 | $10^{-7}$ M | Lackey et al, 2000, Bioorg. Med. Chem. Lett. 10: 223-226 |
| AG490 | Stat3 | $10^{-5}$ M | Sharfe et al., 1995, Blood 86: 2077-2085 |
| LY294002 | PI3K | $10^{-5}$ M | Saward et al., 1997, Circ. Res. 81: 249-257 |
| AG1024 | Insulin receptor | 0.5 × $10^{-5}$ M | Zahradka et al, 2004, Endocrinology 145: 2978-2987 |
| Pertussis toxin | G-protein | 5 μL/mL | Hsia et al, 1984, J. Biol. Chem. 259: 1086-90 |
| Go7874 | PKA | $10^{-6}$ M | Kleinschroth et al, 1995, Bioorg. Med. Chem. Lett. 5: 55-60 |
| Go6976 | PKA | $10^{-6}$ M | Martiny-Baron et al, 1993, J. Biol. Chem. 268: 9194-9197 |
| Rottlerin | PKC δ | $10^{-6}$ M | Gschwendt et al, 1994, FEBS Lett. 338: 85-88 |

EXAMPLE 1

D-CI, MI, and fagopyritols are concentrated in the testa and embryo of buckwheat groats. However, these seed parts comprise only 25% of the buckwheat groats whereas the major component the groats is the endosperm portion. Accordingly, a milling procedure was developed to isolate a fraction from buckwheat primarily containing the cotyledon, embryo, and testa with only a minimal amount of endosperm.

Buckwheat variety Koto (*Fagopyrum esculentum*, Moench) de-hulled seeds were provided by Kade Research Ltd. (Morden, Manitoba, Canada). First, the moisture concentration was increased from 12 to 17% in dehulled buckwheat seeds 2 hours prior to milling, by the addition of water to the buckwheat seeds. Moisture was then further increased by an additional 1% just prior to milling. The moisturized seeds were milled using a Buhler mill (MLU-202) according to the manufacturer specifications. The grinding gaps were set as follows: B1=11.5, B3=5.5, 1M=6.25, 3M=2. The screen sizes for the breaks were as follows: B1=40 wire (414 microns), B2=40 wire (414 microns), B3=45 wire (323 microns). The screen sizes for all flour sieves were 9xx (153 microns).

Seeds were passed through a series of corrugated roller mills or break rolls followed by sifting to separate the coarse, flexible particles (testa, cotyledon, and embryo) from the fine, dry particles (endosperm). The overs of the break rolls were collected as the bran fraction. The throughs of the break rolls were passed through smooth reduction rolls followed by sifting. The overs of the reduction rolls, or the shorts, were more fine particles of testa, cotyledon, and embryo with some remaining endosperm attached. The throughs of the reduction rolls, or white fraction, were finely ground endosperm particles.

A liquid BWE was produced combining the bran and shorts fractions after which they were ground and then thoroughly homogenized in ethanol:water (1:1, v/v) for 10 minutes (5 volumes of solvent to 1 volume of flour). The homogenate was vacuum-filtered and the remaining residue re-extracted with the same volume of solvent. The filtrates were combined and the solvent was removed by evaporation in a rotary evaporator (Yamato RE200, Orangeburg, N.Y.) under vacuum until a 40-fold reduction in solvent volume was achieved.

Aliquots (100 μL) of the BWE were transferred to silylation vials (Pierce) and evaporated to dryness under nitrogen at 40° C. The dry residues were derivatized as described by Horbowicz et al., 1994, Seed Sci. Res. 4: 385-405, with 1.6 mL of silylation reagent (trimethylsilylimidazole:pyridine, 1:1, v/v, containing 200 μg phenyl-α-D-glucoside) at 75-80° C. for 1 hour.

Two μL of derivatized carbohydrates were injected into a Shimadzu gas chromatograph GC-17A (Columbia, Md.) equipped with a flame ionization detector and split injector. Carbohydrates were separated on a RTX-5MS capillary column (25 m length, 0.25 mm ID, and 0.25 μm film thickness; Restek, Bellefonte, Pa.). Column temperature was programmed from 150° to 200° C. at the rate of 3° C./min, then to 325° C. at the rate of 7° C./min. Initial and final temperatures were held for 5 and 20 minutes, respectively. The injector and detector temperatures were held at 270° C. and 350° C., respectively. The carrier gas was hydrogen at a flow rate of 1.5 mL/min while the split ratio used was 1:40. Soluble carbohydrates including inositols were quantified using phenyl-α-D-glucoside as the internal standard. The data is shown in Table 2.

BWE were analyzed for content of protein using AOAC method 955.04 (AOAC, 1997) and minerals by atomic absorption spectrometry.

The data are shown in Tables 2 and 3.

TABLE 2

BWE composition[a].

| Component | Contribution |
|---|---|
| Carbohydrates | |
| D-chiro-inositol | 0.2% |
| myo-inositol | 0.1% |
| Sucrose | 6.0% |
| Fagopyritols | 5.7% |
| Protein | 5.0% |
| Minerals | |
| Calcium | 130 ppm |
| Iron | 2 ppm |
| Magnesium | 900 ppm |
| Manganese | 2 ppm |
| Phosphorous | 2800 ppm |
| Selenium | 26 ppm |
| Zinc | 60 ppm |

[a]Amount in BWE administered as "high-dose" for functional assessments (i.e., 20 mg D-CI/kg body weight). "Low-dose" BWE was prepared by diluting the high-dose BWE 2-fold (i.e., 10 mg D-CI/kg body weight).

TABLE 3

Sugar content in BWE.

| Component | Concentration (mg/mL) |
|---|---|
| fructose | 122 |
| glucose | 107 |
| D-chiro-inositol | 10.3 |
| myo-inositol | 10 |
| sucrose | 158 |
| raffinose | 2 |
| stachyose | 2 |

EXAMPLE 2

The objectives of the study outlined in this Example were to assess the effects of the two dosage levels BWE from Example 1 on elevated serum glucose levels and glucose tolerance by using an oral glucose tolerance test (OGTT; provides a functional measurement of whole body glucose tolerance) to measure BWE effects on glucose tolerance in fasted normal (i.e., control) rats and on hyperglycemia in STZ (i.e., diabetic) rats.

The myo-inositol standard, phenyl-α-D-glucoside (internal standard), trimethylsilylimidazole, pyridine, and streptozotocin (STZ) were purchased from Sigma Chemical Co. (St. Louis, Mo.). Reagent alcohol was purchased from Fisher Scientific Co. (Ottawa, Ontario, Canada, K2E 7L6). D-chiro-inositol standard was a gift from Dr. S. G. Angyal (University of New South Wales, Australia).

Fifty-two male Sprague-Dawley rats (Central Animal Holding, Winnipeg, Manitoba, Canada) weighing 150-180 grams were acclimatized for a period of 7 days. Throughout the acclimatization and subsequent study period, rats were maintained in a controlled environment of 21-23° C., 55% humidity, and a 14-hour light, 10 hour dark cycle. Rats were housed in groups of two in plastic hanging cages, fed standard laboratory chow (Prolab RMH 3000, Purina Mills, Richmond, Ind., USA) ad libitum and fresh water was available in polypropylene bottles with stainless steel sipper tubes. Rats were familiarized with subsequent testing procedures during this adaptation period. A protocol for animal care procedures was approved by the University of Manitoba Protocol Management and Review Committee.

Treatments were a single delivery of a low-dose BWE (10 mg D-CI/kg body weight), a high-dose BWE (20 mg D-CI/kg body weight), a low-dose placebo (3% sucrose:dionized water solution), or a high-dose placebo (3% sucrose:dionized water solution).

Following the acclimatization period, 12 male Sprague-Dawley rats were randomly assigned to either the low-dose BWE group or the low-dose placebo group. The protocol for treatment and sampling from the control animals is shown in FIG. 2(i). The control animals received either the low-dose placebo or high-dose placebo and then, were fasted for 2 hours after which an intraperitoneal glucose tolerance test (IPGTT) was conducted by collecting blood from the saphenous vein for the 0-min time point. Immediately following, a 70% glucose solution was injected intraperitoneally (4 g glucose/kg body weight) into each control animal. Blood was collected from the saphenous vein at 30, 60, 90, and 120 minutes from the time of the initial glucose administration. Blood samples were held on ice until centrifuged to obtain serum. Serum samples were stored at −20° C. until analysis.

Following the acclimatization period, 40 randomly-selected rats received intraperitoneal injections of 60 mg STZ/kg body weight/day on day 1 and 2 of the experiment. STZ was freshly dissolved in 0.9% NaCl, pH 5.5 at a concentration of 15 mg/mL. Three days after the second injection, a blood sample to measure blood glucose levels was taken via the saphenous vein. Diabetes was defined when a blood glucose concentration of 13 mmol/L or greater was achieved. Rats with a positive response to STZ administration were randomly assigned to the low-dose BWE, high-dose BWE, low-dose placebo, or high-dose placebo groups. Rats were individually housed for the remainder of the experiment. The protocols for treatment and sampling from diabetic STZ rats are shown in FIGS. 2(ii) and 2(iii).

The first test procedure performed on the group of STZ rats treated with the protocol shown in FIG. 2(ii), was on day 7 of the experiment. Blood was collected via the saphenous vein for the 0 time point and immediately following, either a buckwheat concentrate or a placebo was administered intragastrically to fed rats. Blood samples were also collected at 30, 60, 90, and 120 minutes following treatment administration.

The first test procedure performed on the group of STZ rats treated with the protocol shown in FIG. 2(iii), was on day 14 of the experiment. After 4 hours of fasting, rats were given intragastrically either a BWE or placebo treatment. One hour following treatment, blood was collected via the saphenous vein for the 0 time point. Immediately following, rats received 1 g glucose/kg body weight (70% glucose solution) intragastrically. Blood was collected at 30, 60, 90, and 120 minutes after administration of glucose. For both tests, blood samples were held on ice until centrifuged to obtain serum. Serum samples were stored at −20° C. until analysis.

Glucose in the serum was assessed in triplicate using an enzymatic colorimetric kit (Procedure #315, Sigma Chemical Co., St. Louis, Mo., USA).

Statistical significance between buckwheat and placebo groups was determined by Student's t test using SAS Statistical Software (v. 8.2, SAS Institute Inc., Cary, N.C.). For effects over time within each treatment group, repeated measures ANOVA was used. Data are expressed as the mean±SE.

Figure 3:
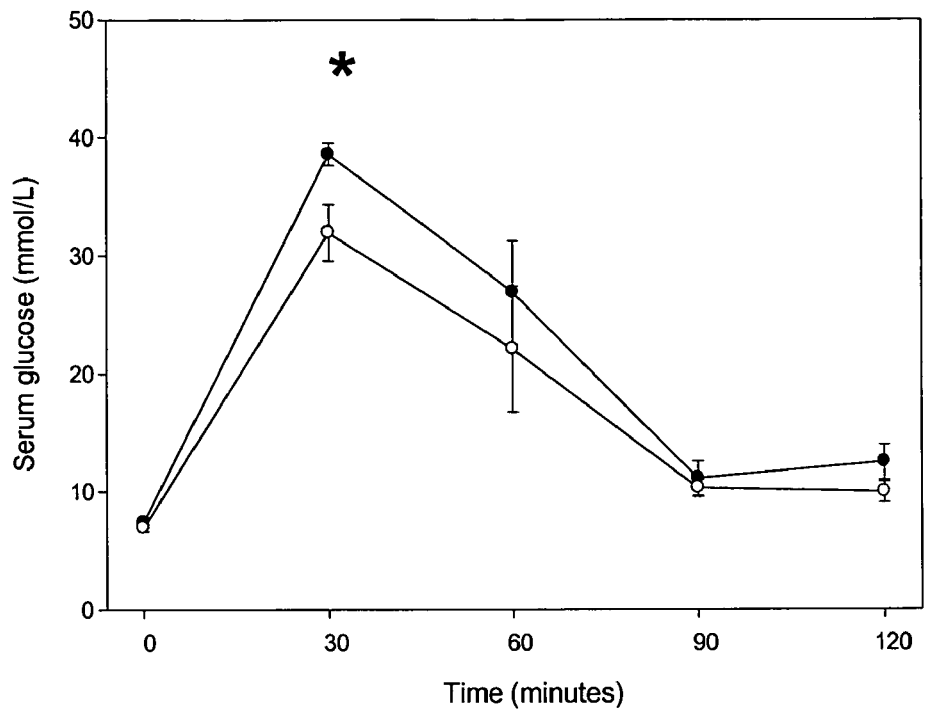
FIG. 3 shows the serum glucose concentrations during an intraperitoneal glucose tolerance test given two hours following administration of a low-dose BWE (10 mg D-chiro-inositol/kg body weight) or placebo in normal rats. Solid circles represent the placebo low dose (n=6) and open circles represent the low-dose BWE (n=6) groups. An * indicates differences (p<0.05) between placebo-treated and buckwheat-treated rats.
Figure 4:
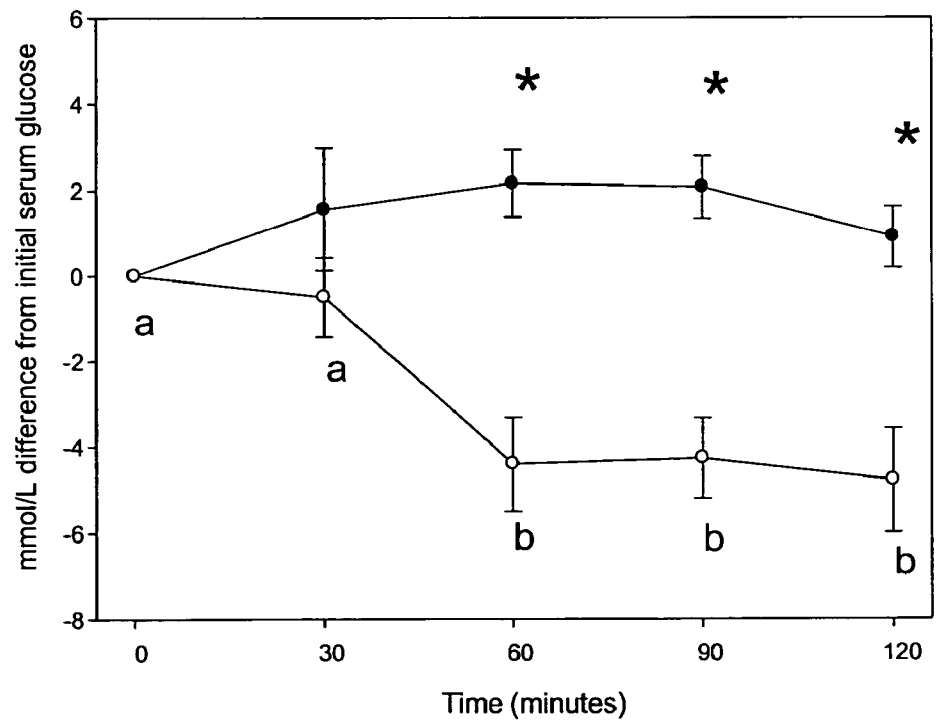
FIG. 4 shows effects of a low-dose of BWE (10 mg D-chiro-inositol/kg body weight) or a placebo given to STZ rats in the fed state on serum glucose concentrations. Data are expressed as the mmol/L difference from initial serum glucose concentrations (28.4±0.95 mmol/L) for the low-dose placebo (solid circles, n=9) and the low-dose BWE (open circles, n=8) groups. An * indicates differences (p<0.001) between placebo-treated and BWE-treated rats. Data points with different letters indicate differences (p<0.05) within a group as determined by Duncan's multiple range test.
Figure 5:
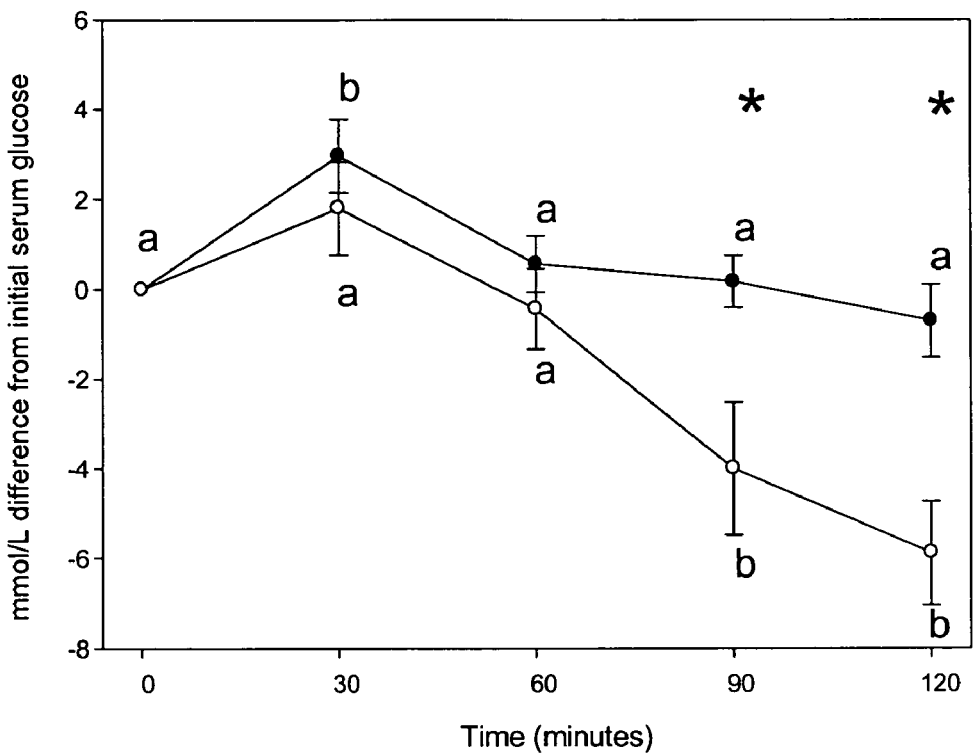
FIG. 5 shows the effects of a high-dose BWE (20 mg D-chiro-inositol/kg body weight) or a high-dose placebo given to STZ rats in the fed state on serum glucose concentrations. Data are expressed as the mmol/L difference from initial serum glucose concentrations (29.6±0.7 mmol/L) for the high-dose placebo (solid circles, n=10) and the high-dose BWE (open circles, n=9) groups. An * indicates differences (p<0.05) between placebo-treated and BWE-treated rats. Data points with different letters indicate differences (p<0.05) within a group as determined by Duncan's multiple range test.

FIG. 3 shows that administration of the low-dose BWE to normal rats 2 hours prior to an IPGTT resulted in serum glucose concentrations that were 17% lower 30 minutes after glucose administration compared to rats given the low-dose placebo. FIG. 4 shows that the low-dose BWE group had a 14-16% decrease in serum glucose concentrations 60 to 120 minutes after treatment administration. In contrast, rats given the low-dose placebo showed 4-10% increases in serum glucose concentrations after 60 to 120 minutes (FIG. 4). The high-dose BWE also reduced serum glucose concentrations in fed STZ rats by 12% after 90 minutes and by 19% after 120 minutes (FIG. 5). In rats given the high-dose placebo, serum glucose concentrations were similar to baseline values after 60 to 120 minutes (FIG. 5).

Figure 6:
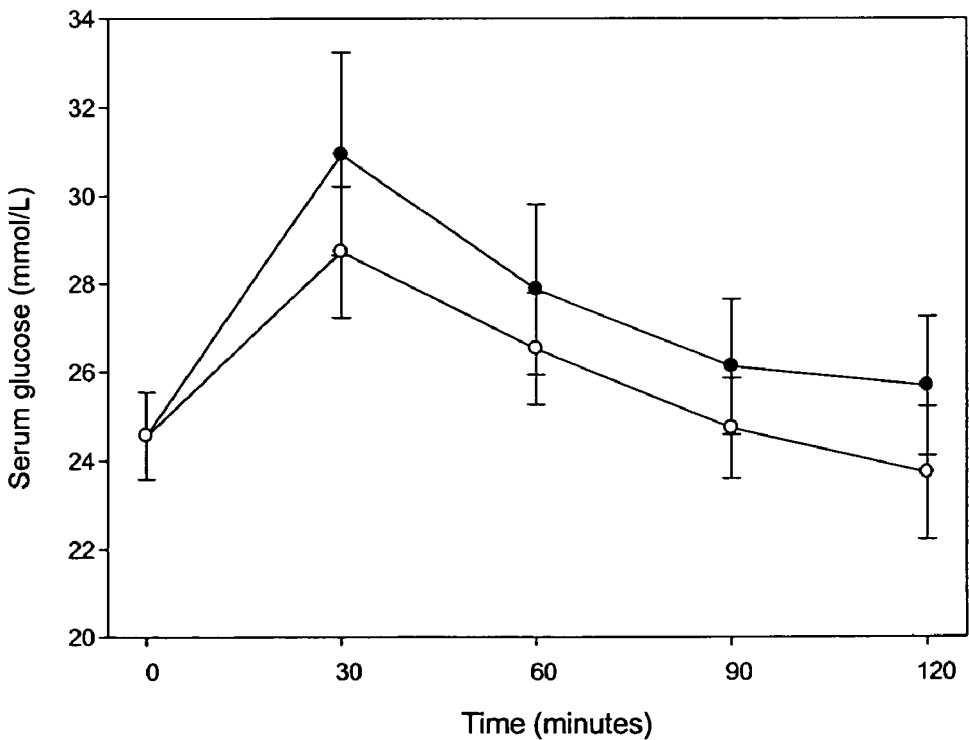
FIG. 6 shows the effects of serum glucose concentrations during an oral glucose tolerance test given one hour following administration of a low-dose BWE (10 mg D-chiro-inositol/kg body weight) or low-dose placebo in fasted STZ rats. Solid circles represent the low-dose placebo (n=9); open circles represent the low-dose BWE (n=8) group.
Figure 7:
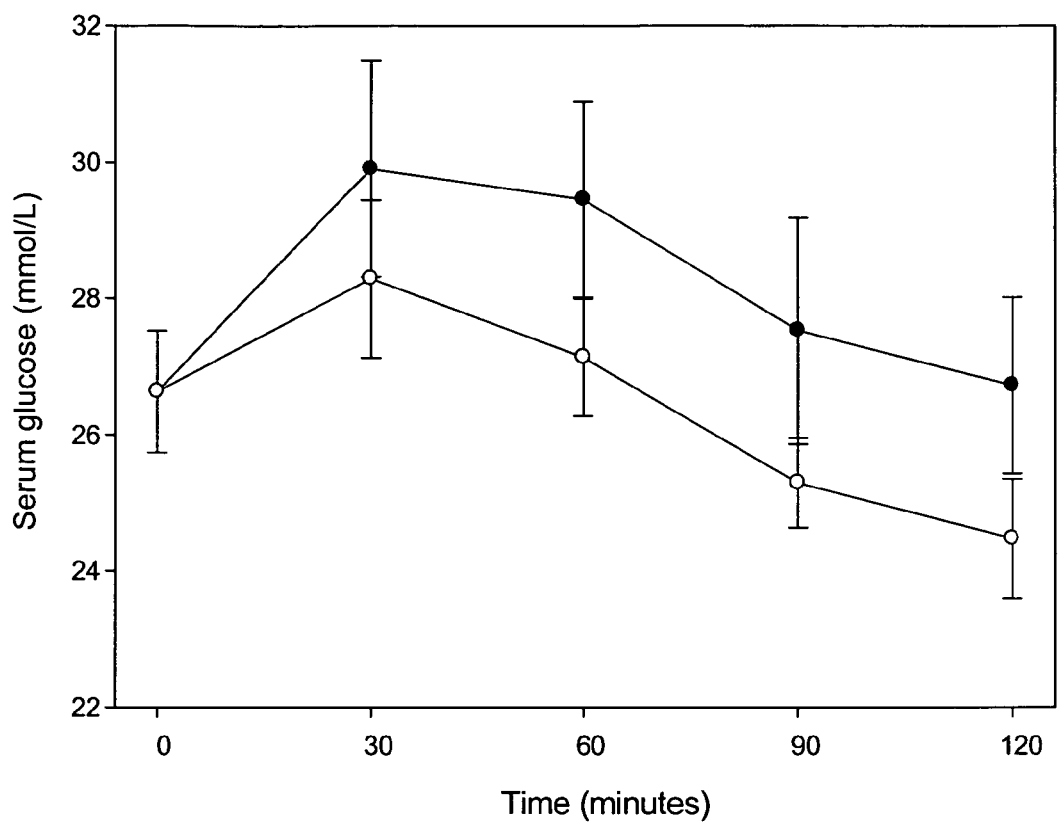
FIG. 7 shows the effects of serum glucose concentrations during an oral glucose tolerance test given one hour following administration of a high-dose BWE (20 mg D-chiro-inositol/kg body weight) or high-dose placebo in fasted STZ rats. Solid circles represent the high-dose placebo (n=10); open circles represent the high-dose BWE (n=9) groups.

FIGS. 6 and 7 show that administration of the BWE to fasted rats prior to an oral glucose tolerance test did not affect serum glucose concentrations. Comparisons of the mean serum glucose concentrations in rats receiving the low-dose BWE (FIG. 6) and high dose BWE (FIG. 7) indicated that the treatments were not statistically significant.

The major finding of the present study was that a single oral dose of the BWE of the present invention was effective in lowering elevated serum glucose concentrations in fed STZ rats. In fed STZ rats, both doses (10 and 20 mg D-CI/kg body weight) of the BWE were effective in lowering serum glucose concentrations by 12-19% at 90 and 120 minutes after treatment administration. The glucose-lowering effects of the BWE treatments in the present study are of magnitudes comparable to data previously disclosed in prior art reports pertaining to synthesized D-CI, thereby suggesting that D-CI in the buckwheat concentrate (Table 2) may be primarily responsible for the observed effects. The BWE of the present invention also contained MI (Table 2); MI is a component of an IPG with insulin-mimetic effects. However, prior art disclosures suggest that administration of synthetic MI has no effects on plasma glucose concentrations. The BWE of the present invention also contained fagopyritols (Table 2). While the role(s) of these D-CI derivatives is not yet known, it appears that the contribution of fagopyritols to the glucose-lowering effects of the BWE observed in the present study is minimal.

The mechanism by which administration of D-CI acts to lower plasma glucose is unknown. Ortmeyer et al. (1993, Endocrinology 132: 646-651) and Fonteles et al (2000, Hormone Metabol.Res. 32: 129-132) suggested that acute administration of D-CI may act to lower plasma glucose by being incorporated into a mediator precursor. Sanchez-Arias et al. (1992, Endocrinology 131:1727-1733) demonstrated that STZ rats have impaired GPI-dependent insulin signaling. Isolated hepatocytes from STZ rats had lower amounts of GPI compared to control rats. STZ-induced diabetes also blocked the hydrolysis of GPI in response to insulin and markedly reduced the uptake of IPG. We have previously reported that urinary D-CI excretion is elevated 336-fold in STZ rats compared to normal rats (Kawa et al., 2003, Exp. Biol. Med. 228: 907-914). This pattern of inositol excretion may be related to altered GPI-IPG signaling system. It is possible that administration of D-CI corrects the GPI-dependent signaling defect of STZ rats. STZ rats are a model of type 1 diabetes mellitus (DM-1), characterized by hyperglycemia and hypoinsulinemia. Insulin deficiency in DM-1 leads to a decrease in glucose utilization by the liver, muscle, and adipose tissue and an increase in hepatic glucose production (Alemzadeh et al., 2002, Eur. J. Endocrinol. 146: 871-879). The antihyperglycemic effect of D-CI may result from inhibition of hepatic glucose output or enhanced glucose transport, glucose utilization, glucose disposal or glycogen synthesis. The mechanism by which administration of D-CI lowers serum glucose concentrations still needs to be established.

The results from this study suggest that an acute dose of D-CI is only effective under specific conditions. Administration of D-CI promoted a decrease in serum glucose concentrations when STZ rats were in the fed state, but did not improve glucose tolerance of fasted STZ rats. To date, this is the first study to report the acute effects of D-CI given to fasted STZ rats prior to an OGTT. In the present study, D-CI can be effective despite subsequent glucose administration in normal rats. Similarly, Ortmeyer et al. (1993) demonstrated that in normal rats, synthetic D-CI administered intragastrically 2 hours before an intraperitoneal glucose load (4 g/kg) produced a 30-50% decrease in plasma glucose. It is possible that administration of glucose to a diabetic animal may compromise the effects of D-CI. Shaskin et al. (1997, Diabetologia 40:557-563) reported that the activity of the IPG containing D-CI increased following glucose ingestion in healthy men whereas no difference in IPG activity was observed in men with Type 2 diabetes. Determining the mechanism by which D-CI lowers serum glucose in the fed state may also elucidate why D-CI is ineffective in fasted rats given a glucose load.

EXAMPLE 3

The purpose of the present study was to evaluate potential mechanisms for the glucose-lowering effects of the BWE in relation to insulin and IPGs. Rat H4IIE hepatoma cells were used in the present study to characterize the role of the BWE in insulin-dependent signaling systems shown in FIG. 1, because it is well known that insulin is able to stimulate glucose metabolic pathways in this cell line. Thus, the objectives of this research were to determine the effects of BWE versus insulin on phosphorylation of signal transduction proteins and to determine which cell signaling pathways were activated by BWE in rat H4IIE hepatoma cells and in rat FAO hepatoma cells.

Tissue culture media, antibiotics, fetal bovine serum (FBS) and Nunc tissue culture plates were purchased from Invitrogen Canada Inc. (Burlington, Ontario, Canada, L7P 1A1). Insulin (Sigma-Aldrich Canada Ltd., Oakville, Ontario, Canada, L6H 6J8) was dissolved in water and added directly to cells at a concentration of 250 nM unless otherwise indicated. The BWE was prepared and analyzed as described in Example 1. Two µL of the BWE were added directly to cells unless otherwise indicated. This amount was chosen on the basis of equivalence to insulin. Myo-inositol (Sigma-Aldrich Canada Ltd.) and D-chiro-inositol (Industrial Research Ltd., Wellington, New Zealand) were dissolved in water at an equal concentration to the amounts present in the BWE (Table 3) and 2 µL of each solution (0.1% v/v final concentration) was added directly to cells.

The polyclonal antibodies against phospho-Akt (Ser$^{473}$), phospho-AMPK (Ser$^{108}$), phospho-ELK-1 (Ser$^{383}$), phospho-GSK3 (Ser$^{21/9}$), phospho-Insulin receptor (Tyr$^{1146}$), p42/44 MAPK, phospho-p42/44 MAPK (Thr$^{202}$/Tyr$^{204}$), phospho-p70$^{S6K}$ (Thr$^{389}$ and Thr421), phospho-PDK-1 (Ser$^{241}$), phospho-PRK1 (Thr$^{778}$), phospho-Raf (Ser$^{259}$), phospho-STAT3 (Tyr$^{705}$) and phospho-S6 ribosomal protein (Ser$^{235/236}$) were purchased from Cell Signaling Technology Inc. (Danvers, Mass., USA 01923). The polyclonal antibody against phospho-Src (Tyr$^{527}$) was obtained from Biosource International Inc. (supplied by Invitrogen Canada Inc.), and phospho-Insulin receptor substrate-I (Tyr$^{941}$) was obtained from Oncogene Science Inc. (Uniondale, N.Y., USA). The HRP-coupled anti-(rabbit IgG) was purchased from Bio-Rad Laboratories (Canada) Inc. (Mississauga, Ontario, Canada L4Z 1N9).

Compounds used as selective inhibitors of signal transduction were obtained from EMD Biosciences Inc. (i.e., Pertussis toxin, Raf kinase inhibitor, Go 7874, AG1024; supplied by VWR CANLAB, Mississauga, Ontario, Canada, L5N 5Z7), New England Biolabs Inc. (i.e., PD98059; Ipswich, Mass., USA, 01938-2723), BIOMOL International LP (i.e., LY294002, AG490, Go 6976, PP1, Rottlerin, U73122; Plymouth Meeting, Pa., USA 19462) and Sigma-Aldrich Canada Ltd (i.e., Brefeldin A, 1-butanol, and 2-butanol). Inhibitor details are provided in Table 1.

The BCA protein assay kit was obtained from Pierce Biotechnology Inc. (Rockford, Ill., USA, 61105). Bovine serum albumin (BSA, fraction V) was purchased from Roche Diagnostics Canada (Laval, Quebec, Canada). Polyvinylidenedifluoride (PVDF) membranes were obtained from Millipore Corp. (Bedford, Mass., USA). The ECL chemiluminescent detection system was provided by Amersham Biosciences (Baie d'Urfe, Quebec, Canada, H9X-3V1). General laboratory chemicals were purchased from Sigma-Aldrich Canada Inc. and Fisher Scientific Co. Ultrapure chemicals (Tris, glycine, SDS, acrylamide, glycerol, Tween 20) were obtained from Invitrogen Canada Inc., Bio-Rad Laboratories, and Roche Diagnostics Canada.

Rat H4IIE hepatoma cells (American Type Culture Collection, CRL 1548) were cultured following the method disclosed by Yau et al., (1998, Eur. J. Biochem. 253: 91-1). The H4IIE cells were maintained in α-modified Eagle's media containing 10% FBS, 2 mM glutamine, 25 µg·mL$^{-1}$ streptomycin and 25 units·mL$^{-1}$ penicillin. Cells were plated and grown to 70% confluence. All cells were placed into serum-free medium for 72 h before addition of stimulating agents to ensure entry into a quiescent state.

FAO cells are related to H4IIE since both cell lines were derived from Reuber H35 cells (Richardson et al., 1969, J. Cell Biol. 40: 236-247). It is known that rat FAO hepatoma cells exhibit a number of hepatocyte-specific differentiation markers and remain sensitive to insulin. FAO hepatoma cells were propagated under the same culture conditions used for H4IIE cells. Quiescent FAO cells were obtained by placing the cells into serum-free medium for 3 days.

Cultures of quiescent H4IIE cells or quiescent FAO cells were placed into 12-well culture dishes containing 2 mL serum-free medium, and then stimulated by direct addition of the inhibitors listed in Table 1 (volumes of additions were 10 µL or less without replacing the medium. Inhibitors were added 10 minutes before the stimulating agents except for pertussis toxin which was added 4 hours prior. The cells in 12-well culture dishes were incubated with stimulating agents for 6 minutes and rinsed with phosphate buffered saline (PBS; 0.9% NaCl, 0.1 M Na$_3$PO$_4$, pH 7.1).

Cellular protein extracts were prepared by addition of 200 µL 2×SDS/gel loading buffer (0.125 M Tris pH 6.8, 2% SDS, 10% glycerol) to H4IIE cells in 12-well culture dishes. The samples were briefly sonicated, and protein content measured using the BCA protein assay kit. Aliquots containing equal amounts of protein were mixed with bromophenol blue (0.5% (w/v) final concentration) and 2-mercaptoethanol (5% (v/v) final concentration), heated at 95° C. and loaded onto 7.5% or 10% polyacrylamide gels. After electrophoresis, the proteins were transferred to PVDF membrane and the membranes subsequently blocked in 3% (w/v) BSA-TBST. Primary antibodies (diluted 1:1000 in 3% (w/v) BSA) were incubated with the membrane for 60 min at 22° C. Membranes were subsequently washed four times and incubated for an additional 60 min at 1 8-22° C. in 1% (w/v) BSA-TBST with diluted HRP-coupled secondary antibody (1:10 000). HRP was detected using the ECL chemiluminescent system after the membranes had been washed four times.

Quantification of data obtained on film (Kodak X-omat) was accomplished with a GS800 imaging densitometer (Bio-Rad Laboratories) under nonsaturating conditions with local background subtraction. Although multiple exposures were acquired to ensure the absence of film saturation, the experimental figures typically show longer exposures selected specifically for visual presentation and not necessarily used for data analysis. Graphical data are presented as means±SE for a minimum of three replicate samples.

Statistical significance between treatment groups was determined using a mixed model analysis with a random intercept for the repetitions (SAS v.8.2, SAS Institute, Cary, N.C.) and by estimate statements for individual comparisons of treatments versus the control. Differences were accepted as significant at p<0.05. Data are expressed as the mean ±SE.

The data from Example 2 show that the BWE of the present invention effectively lowered serum glucose concentrations in STZ rats. In order to determine the mechanism by which the BWE lowers serum glucose, we examined its effects on key processes activated by insulin in H4IIE cells. The effects of BWE on protein phosphorylation within the various insulin-stimulated cell signaling pathways were investigated in the present study, specifically the proteins listed within the shaded circles in FIG. 1.

To assess the intracellular signaling pathways that contribute to the actions of the BWE, we evaluated the effects of inhibiting phospholipase D (PLD), Src kinase (Src), and Arf3 on the ability of INS and the BWE to subsequently stimulate selected signal transduction proteins. FIG. 16($i$) shows the band intensities for phosphorylation of InsR and MAPK by insulin and the BWE when PLD, Src, and Arf3 were inhibited. Phosphorylation of InsR was stimulated by insulin only, and PLD, Src, and Arf3 were not required (FIG. 16($ii$)). The BWE did not stimulate phosphorylation of InsR, the same as the result shown in FIG. 8($i$). As shown in FIG. 16($iii$), both insulin and the BWE stimulate MAPK phosphorylation. PLD (butanol sensitive) is required for stimulation of MAPK by insulin and the BWE, whereas Src (PP1 sensitive) is required for stimulation of MAPK by the BWE only. Arf3 (brefeldin sensitive) is not involved in this process.

The effects of other inhibitors (Table 1) on insulin- and BWE-stimulated phosphorylation of MAPK, PDK1 and Raf, were also determined. Insulin- and BWE-dependent stimulation of MAPK phosphorylation were inhibited by PD98059 (Tables 4, 5, & 6) whereas no other inhibitors had any effects. These data indicate that G-protein, PI3K, Stat3, InsR, Raf, PLC, PKA and PKC are not required for MAPK phosphorylation by insulin or the BWC in H4IIE cells. Phosphorylation of PDK1 and Raf was not stimulated by either insulin or the BWE, and subsequently none of the inhibitors had any effects on these proteins.

TABLE 4

Effects of inhibitors on insulin-stimulated phosphorylation of selected signal transduction proteins[a].

| Antibodies | Inhibitors | | | | | | | |
|---|---|---|---|---|---|---|---|---|
| | None | PTX | LY | PD | AG490 | AG1024 | Raf | U73 |
| p42/44 P-MAPK (Thr$^{202}$/Tyr$^{204}$) | 13.3 | 11.2 | 10.4 | 1 | 16.4 | 16.74 | 17.7 | 13.4 |
| PDK-1 (Ser$^{241}$) | 1.57 | 1.71 | 1.40 | 1.89 | 1.91 | 2.30 | 1.79 | 2.30 |
| Raf (Ser$^{259}$) | 0.53 | 0.29 | 0.22 | 0.20 | 0.13 | 0.26 | 0.29 | 0.99 |

[a]Following a 15-min preincubation with the indicated inhibitors, H4IIE cells were treated with insulin for 6 minutes with untreated cells serving as the control. Concentrates were subsequently prepared for Western blot analysis. Band intensities on each blot were quantified by scanning densitometry and are presented as stimulation (fold) relative to the control. The values for the control are 1.00 and data presented are from one experiment.

Figure 8:
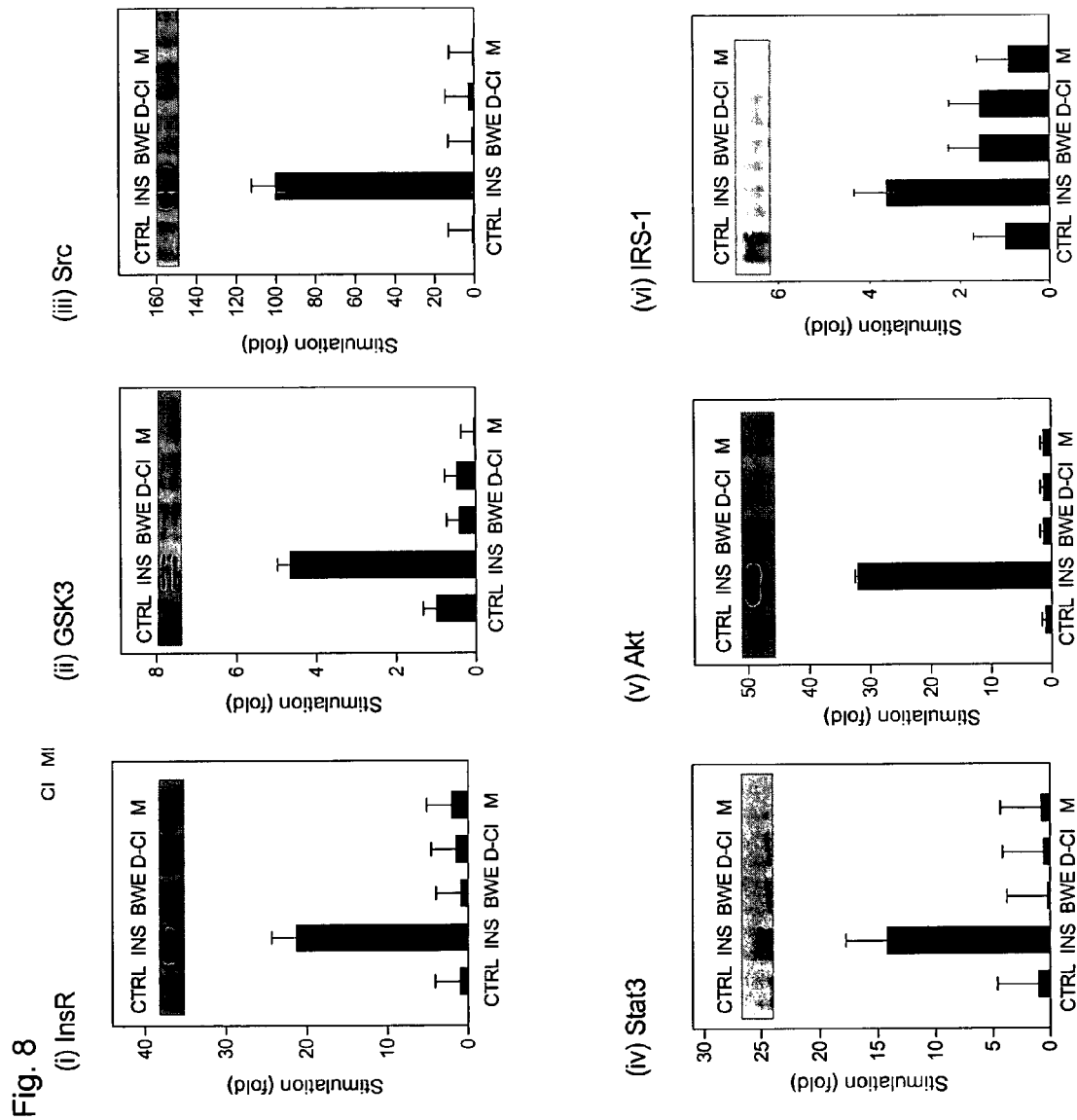
FIG. 8 shows the effects of insulin (INS), BWE, D-chiro-inositol (D-CI) and myo-inositol (MI) on phosphorylation of select signal transduction proteins assessed by Western blot analysis. H4IIE cells were treated with each agent individually for 6 minutes, with untreated cells serving as the control (CTRL). Each experiment was replicated three times. Band intensities on each Western blot were quantified by scanning densitometry and plotted as means ±SE (n=3). Significant differences (p<0.05) between treatments versus the control (*) are indicated. The p-value for the comparison of insulin-stimulated phosphorylation of Stat3 versus the control was p=0.06.
Figure 9:
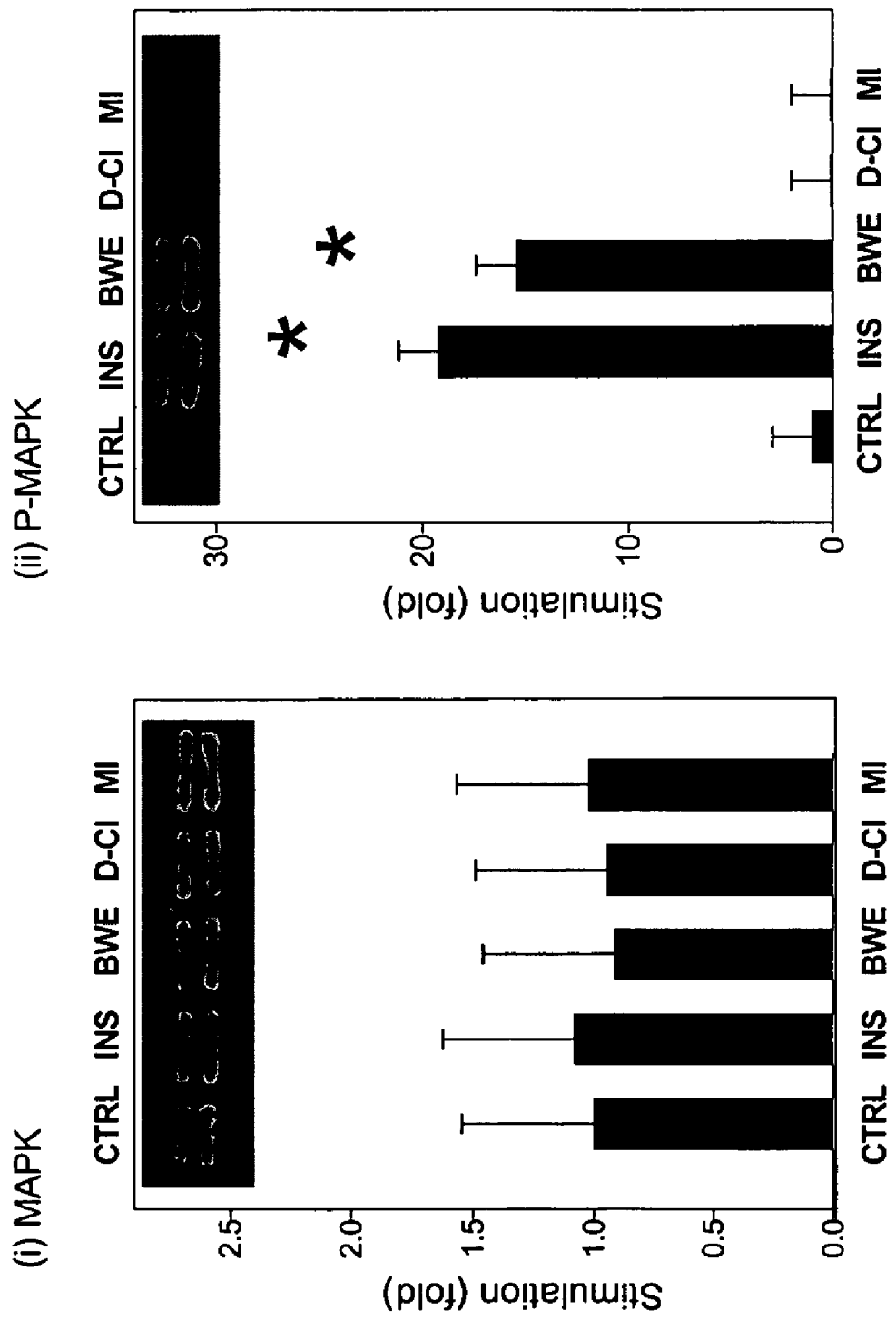
FIG. 9 shows the effects of insulin (INS), BWE, D-chiro-inositol (D-CI) and myo-inositol (MI) on stimulation of (i) mitogen-activated protein kinase (MAPK) and (ii) phosphorylated (P-MAPK) assessed by Western blot analysis. H4IIE cells were treated with each agent individually for 6 minutes, with untreated cells serving as the control (CTRL). Each experiment was replicated three times. Band intensities on each blot were quantified by scanning densitometry and plotted as means ±SE (n=3). Significant differences (p<0.05) between treatments versus the control (*) are indicated.
Figure 10:
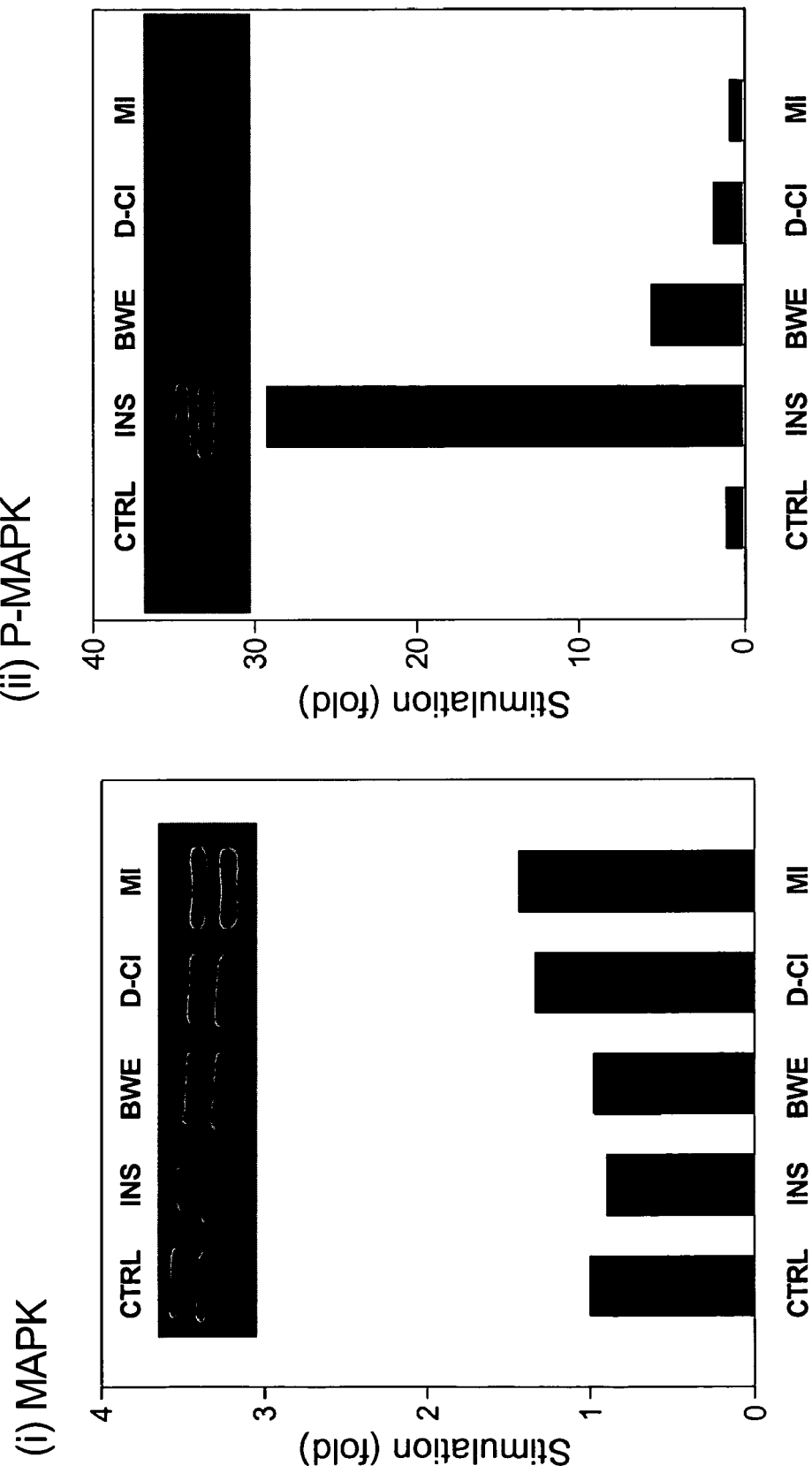
FIG. 10 shows the effects of insulin (INS), BWE, D-chiro-inositol (D-CI) and myo-inositol (MI) on phosphorylation of mitogen-activated protein kinase (MAPK) in FAO cells.
Figure 11:
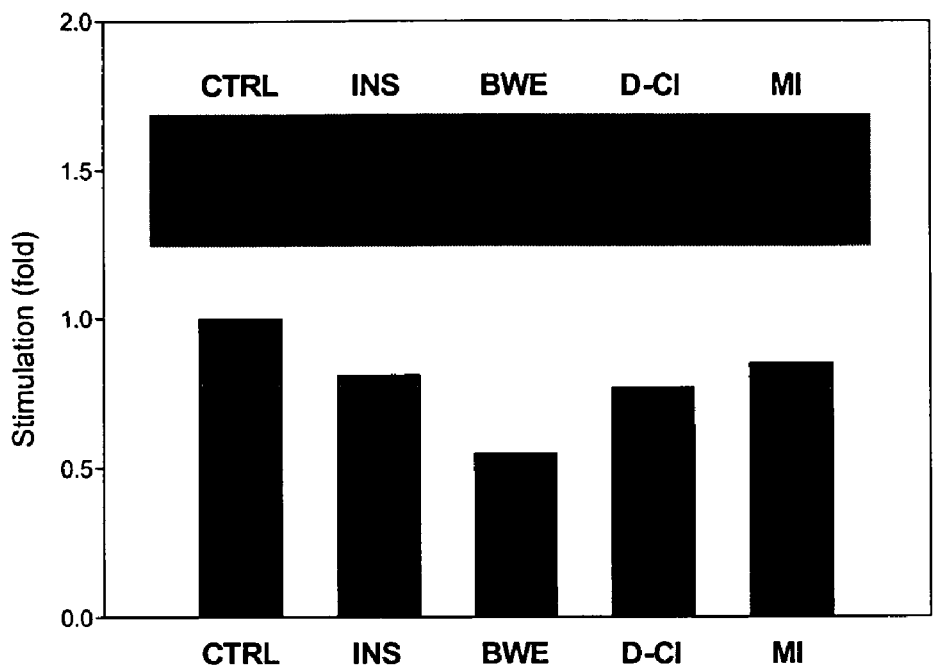
FIG. 11 shows the effects of insulin (INS), buckwheat extract (BWE), D-chiro-inositol (D-CI) and myo-inositol (MI) on phosphorylation of Raf in FAO cells.
Figure 12:
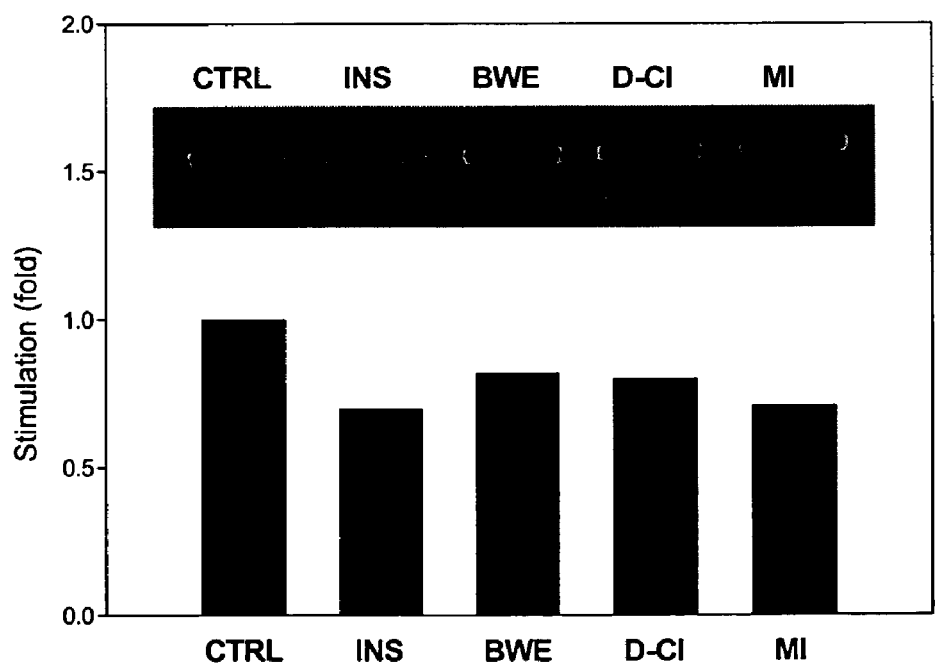
FIG. 12 shows the effects of insulin (INS), BWE, D-chiro-inositol (D-CI) and myo-inositol (MI) on phosphorylation of PDK1 in FAO cells.

FIG. 8 shows that some signal transduction proteins, i.e. InsR, IRS-1, Akt, Src, STAT3 and GSK3, are phosphorylated in response to insulin, while treatments with the BWE, D-CI or MI do not provide comparable stimulation of those proteins. In contrast, both insulin and BWE increased the phosphorylation of MAPK (FIG. 9), while neither D-CI nor MI increased phosphorylation of this protein. To determine if these results were unique to the H4IIE cells, we also evaluated the effects of the BWE on phosphorylation of MAPK in FAO hepatoma cells. The data in FIGS. 10, 11, and 12 show that BWE and insulin also stimulated MAPK phosphorylation in FAO cells whereas D-CI and MI did not.

Figure 13:
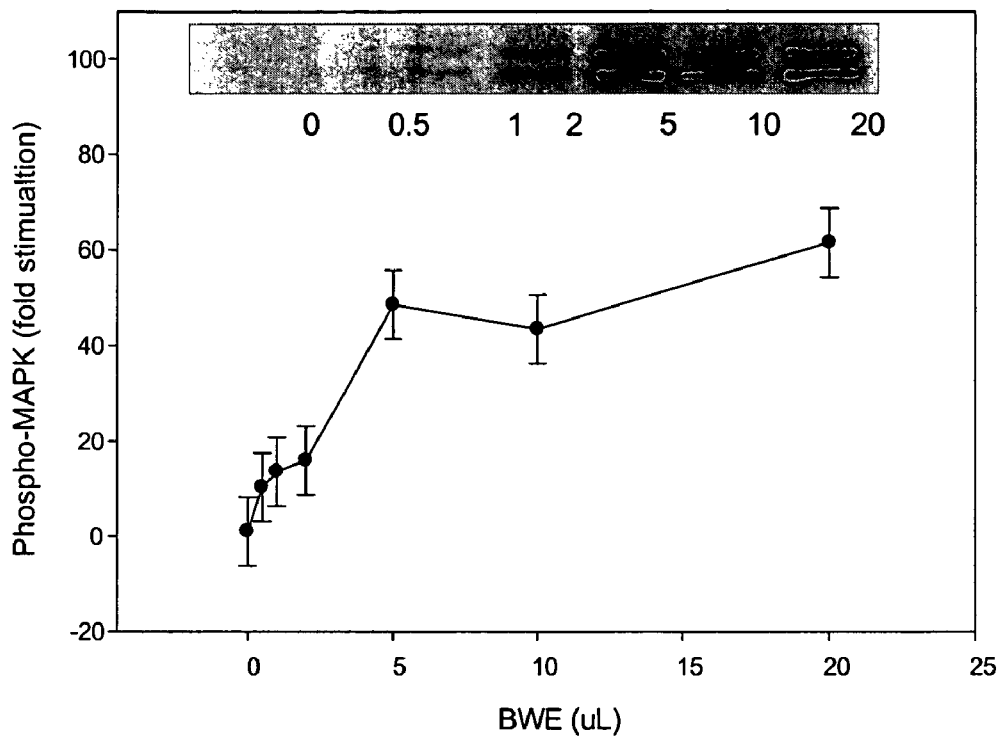
FIG. 13 shows the concentration-dependent effects of BWE on mitogen activated protein kinase (MAPK) phosphorylation assessed by Western blot analysis. H4IIE cells were treated with increasing amounts of BWE individually for 6 minutes. Each experiment was replicated three times. Band intensities on each blot were quantified by scanning densitometry and plotted as means ±SE (n=3). Significant differences (p<0.05) between each BWE amount versus the control (*) are indicated.
Figure 14:
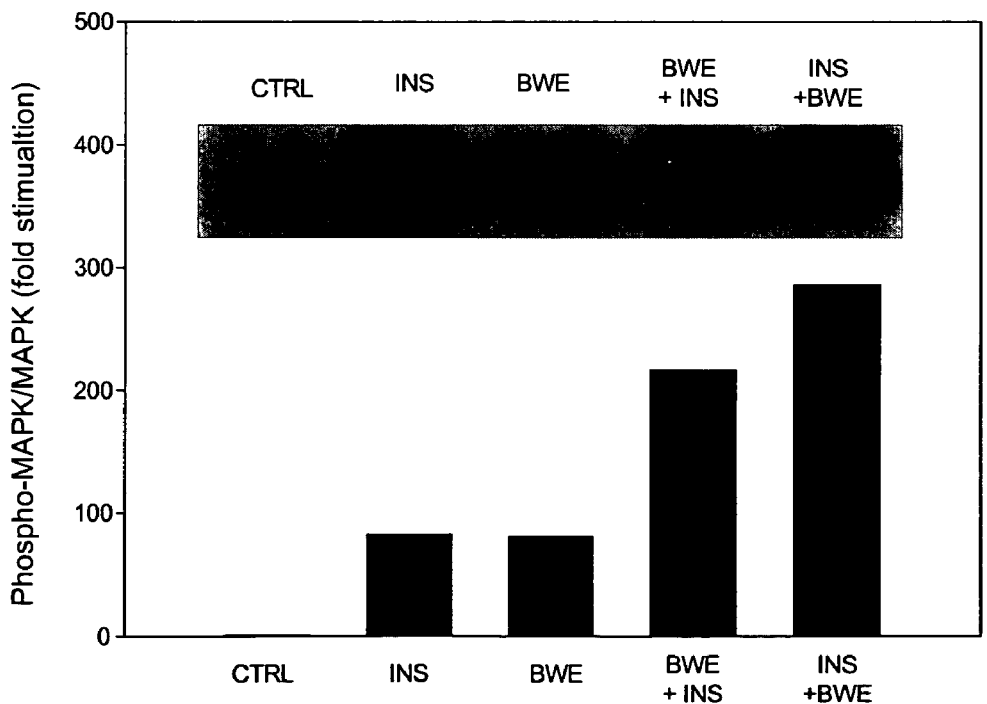
FIG. 14 shows the effects of insulin (INS) and BWE on phosphorylation of mitogen-activated protein kinase (MAPK) assessed by Western blot analysis. H4IIE cells were treated for 6 minutes with INS, BWE or a combination of both where either BWE (BW+I) or INS (I+BW) was added first. Untreated cells served as the control (CTRL). Band intensities were quantified by scanning densitometry.
Figure 15:
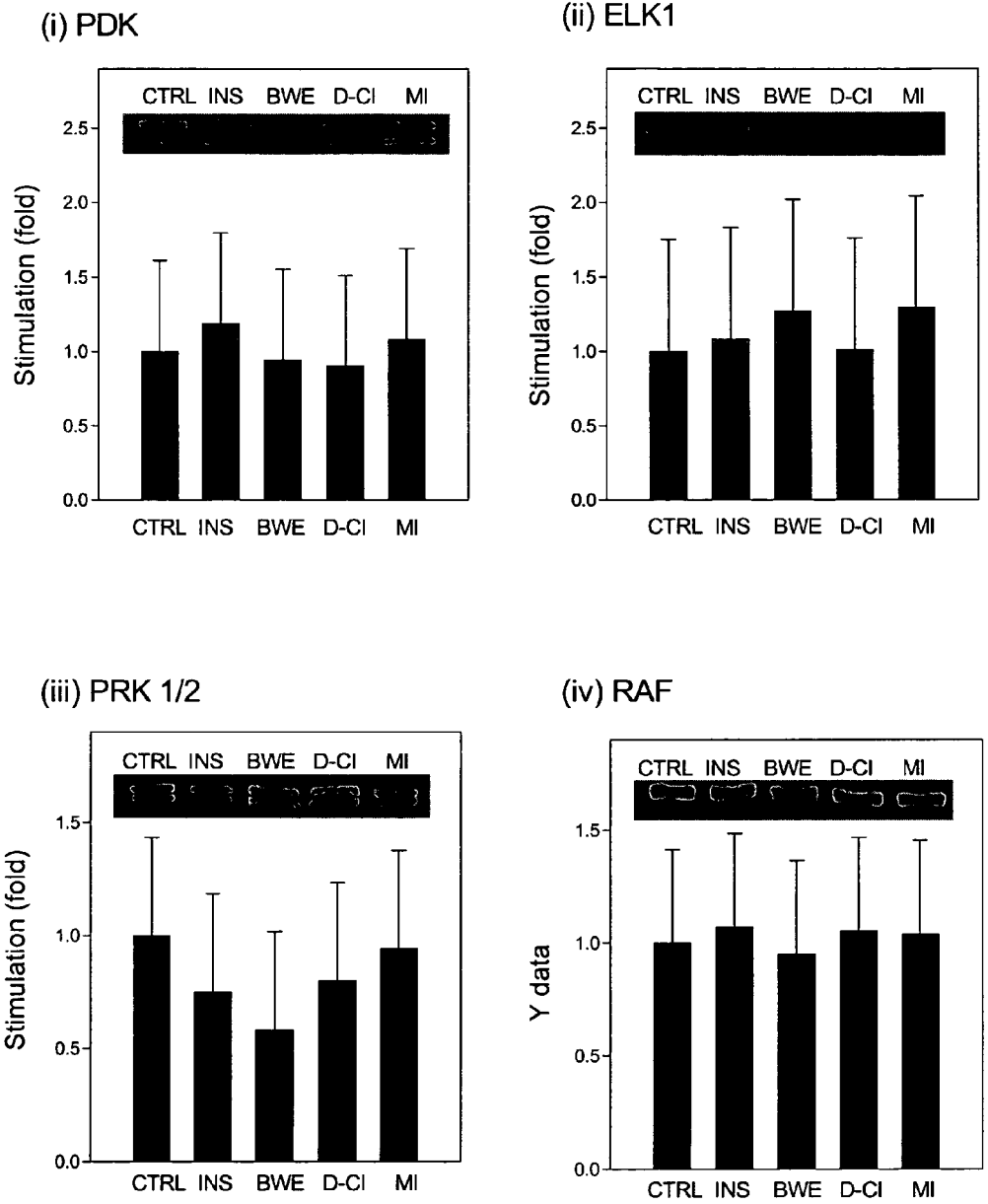
FIG. 15 shows the effects of insulin (INS), BWE, D-chiro-inositol (D-CI) and myo-inositol (MI) on phosphorylation of select signal transduction proteins assessed by Western blot analysis. H4IIE cells were treated with each agent individually for 6 minutes, with untreated cells serving as the control (CTRL). Each experiment was replicated three times. Band intensities on each blot were quantified by scanning densitometry and plotted as means ±SE (n=3)

FIG. 13 shows the concentration-dependent phosphorylation of MAPK by the BWE. Phosphorylation of MAPK was effectively increased by 0.5 µL to 20 µL of the BWE. To determine if insulin and the BWE affect MAPK to a similar degree, the effect of combining these agents was tested. The data shown in FIG. 14 indicate that the effects of insulin and the BWE on MAPK are additive. FIG. 15 shows that the PDK, PRK1/2, RAF and ELK1 proteins were not activated by any of the treatments.

TABLE 5

Effects of inhibitors on the BWE-stimulated phosphorylation of selected signal transduction proteins[a].

| Antibodies | Inhibitors | | | | | | |
|---|---|---|---|---|---|---|---|
| | None | PTX | LY | PD | AG490 | Raf | U73 |
| p42/44P-MAPK (Thr$^{202}$/Tyr$^{204}$) | 15.8 | 14.4 | 13.1 | 1.00 | 12.9 | 16.9 | 8.6 |
| PDK-1 (Ser$^{241}$) | 0.82 | 0.58 | 0.61 | 0.54 | 0.89 | 0.27 | 0.49 |
| Raf (Ser$^{259}$) | 0.30 | 0.28 | 0.08 | 0.20 | 0.16 | 0.12 | 0.12 |

[a]Following a 15 minute preincubation with the indicated inhibitors, H4IIE cells were treated with BWE for 6 minutes with untreated cells serving as the control. Concentrates were subsequently prepared for Western blot analysis. Band intensities on each blot were quantified by scanning densitometry and are presented as stimulation (fold) relative to the control. The values for the control are 1.00 and data presented are from one experiment.

TABLE 6

Effects of inhibitors on phosphorylation of mitogen-
activated protein kinase (MAPK) by insulin or BWE[a].

| Treatments | Inhibitors | | | |
|---|---|---|---|---|
| | None | Rottlerin | Go6976 | Go7874 |
| Insulin | 3.53 | 2.46 | 4.68 | 2.60 |
| BWE | 5.27 | 3.85 | 4.32 | 3.10 |

[a]Following a 15 minute preincubation with the indicated inhibitors, H4IIE cells were treated with insulin or BWE for 6 minutes with untreated cells serving as the control. Concentrates were subsequently prepared for Western blot analysis with p42/44 P-MAPK(Thr$^{202}$/Tyr$^{204}$) antibody. Band intensities on each blot were quantified by scanning densitometry and are presented as stimulation (fold) relative to the control. The values for the control are 1.00 and data presented are from one experiment.

Figure 19:
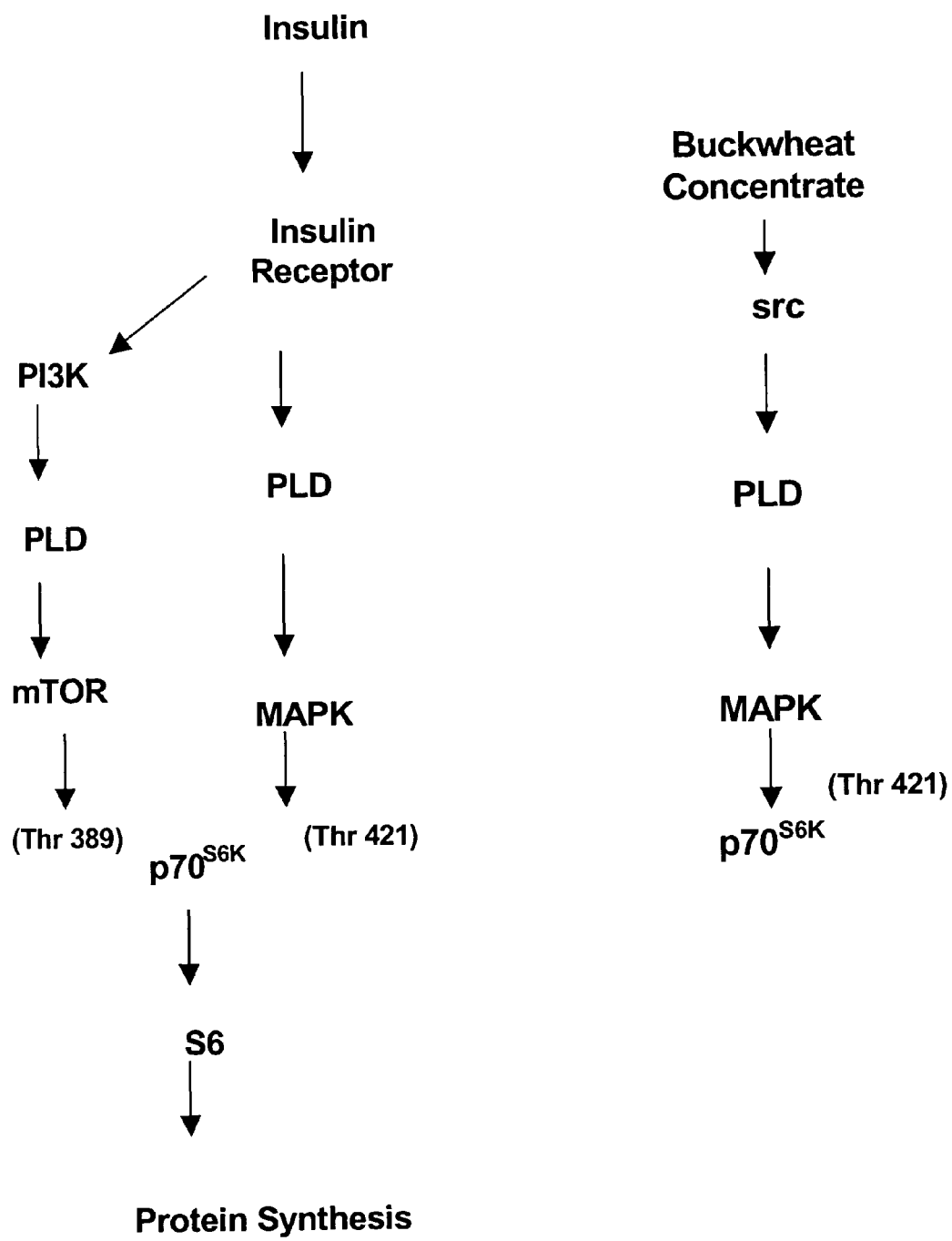
FIG. 19 is a schematic flowchart showing the effects of insulin and the buckwheat concentrate on phosphorylation of signal transduction proteins in H4IIE cells.

The effects of BWE versus insulin on phosphorylation of proteins downstream from MAPK were also assessed in this study. BWE stimulated phosphorylation of p70$^{S6K}$ (Thr$^{421}$) (FIG. 17(i)), but not p70$^{S6K}$ (Thr$^{389}$) (FIG. 17(ii)). In contrast, insulin stimulates the phosphorylation of p70$^{S6K}$ on both residues. Phosphorylation of ribosomal protein S6, which is immediately downstream from p70$^{S6K}$, requires dual p70$^{S6K}$ phosphorylation (FIG. 17(iii)). FIGS. 18(i) and 18(ii) show that stimulation of p70$^{S6K}$ (Thr$^{421}$) by both insulin and the BWE is MAPK-dependent (PD98059 sensitive), but is independent of PI3K (LY294002 sensitive). In contrast, insulin-dependent stimulation of p70$^{S6K}$ (Thr389) phosphorylation requires activation of PI3K but is independent of MAPK (FIG. 18(iii)). A summary of these results is shown in FIG. 19. Other individual pathways leading from the insulin receptor, as shown in FIG. 1, could also be incorporated into this scheme but the lack of effects to BWE suggests they are of no relevance for further investigation.

Insulin activates numerous cell signaling pathways upon binding to its receptor. Among the downstream effects resulting from these pathways are increased glucose The data produced in the present study indicate that the BWE activates uptake, utilization and storage, as well as decreased glucose production and release, increased lipogenesis and protein synthesis (FIG. 1). Insulin mimetic compounds can also stimulate phosphorylation of proteins within these pathways, thus inducing similar biological effects. IPGs containing D-CI and MI have also demonstrated insulin mimetic effects including increased glucose uptake, utilization and storage. However, the results of the present study indicate a separate cell signaling pathway for BWE versus D-CI and MI.

As shown in FIG. 16(iii), both PLD (butanol sensitive) and src (PP1 sensitive) are required for BWE-dependent stimulation of MAPK phosphorylation, whereas only PLD is required for insulin-dependent stimulation of MAPK phosphorylation. PLD is a phospholipid-degrading enzyme that is recognized for its abilitiy to generate biologically active products which are assumed to play important functions in cell regulation (Liscovitch et al., 2000, Biochem. J. 345: 401-415). The interaction of extracellular-signal molecules with cell-surface receptors including insulin often activates a PLD-mediated hydrolysis of phospholipids (Liscovitch et al.). In fact, the release of IPGs from cell membranes in response to insulin is considered to be mediated by PLD (Jones and Varela-Nieto, 1999, Molec. Med. 5:505-514). It is possible that BWE is also involved in this response.

p70$^{S6K}$ is downstream from MAPK and is required for cell growth (Gabele et al., 2005, J. Biol. Chem. 280: 13374-13382). p70$^{S6K}$ also phosphorylates the ribosomal protein S6, which is involved primarily in protein synthesis. The BWE stimulated phosphorylation of p70$^{S6K}$ (Thr$^{421}$) but not p70$^{S6K}$ (Thr$^{389}$), unlike insulin which stimulated phosphorylation of both p70$^{S6K}$ residues. Although the BWE did not stimulate S6 phosphorylation, insulin did, thus indicating the requirement for phosphorylation of both the Thr$^{421}$ and Thr$^{389}$ residues on p70$^{S6K}$ for subsequent phosphorylation of S6. The significance of the BWE-stimulated phosphorylation of p70$^{S6K}$ (Thr$^{421}$) may be related to cell growth or another unknown downstream effect.

Insulin was effective for stimulating phosphorylation of InsR, IRS-1, GSK3, STAT3, src, and Akt unlike the BWE, D-CI, and MI which did not increase phosphorylation of these proteins (FIG. 8). These results indicate that the BWE (D-CI and MI) does not affect glucose metabolism with regards to glycogen synthesis via the Akt/GSK-3 pathway or transcription via the Jak/STAT, PI3K/Akt and PRK/SRF pathways in H4IIE cells. Thus, the BWE, D-CI, and MI should not be able to stimulate lipogenesis and protein synthesis via Akt, or inhibit lipolysis via Akt in this cell type. Results from the present study also indicate that certain signal transduction proteins within insulin signaling pathways are constitutively phosphorylated in H4IIE cells. Among these are PDK, PRK1/2, Raf and ELK1.

In an attempt to elucidate the active component/s of the BWE responsible for the observed effects, we also evaluated the effects of free D-CI and MI on phosphorylation of signal transduction proteins. The insulin-mimetic effects of free D-CI and MI have not been evaluated at the cell signal transduction level. However, free D-CI has demonstrated blood glucose lowering effects in animal models of diabetes presumably through a mechanism related to insulin-like activities of IPGs (Ortmeyer et al., 1993, Endocrinology 132:640-645; Fonteles et al., 2000, Diabetologia 39: 731-734). Unlike the BWE in the present study, D-CI and MI were unable to effect phosphorylation of MAPK or p70$^{S6K}$ (Thr$^{421}$).

Results from the present study demonstrate that BWE has insulin-mimetic effects in H4IIE cells, with respect to phosphorylation of MAPK and p70S6K (Thr$^{421}$) downstream from MAPK and that PLD and src are required. Activation of these cell signal transduction proteins by BWE may be related to the glucose-lowering effects of BWE previously observed in STZ rats. Both insulin and BWE require PLD activation for phosphorylation of MAPK. However, BWE also requires phosphorylation of src (FIG. 16(ii)) despite the lack of BWE-stimulated src phosphorylation (FIG. 8(iii)). The p70$^{S6K}$ protein is downstream from MAPK and its phosphorylation on the Thr$^{421}$ residue was also stimulated by both insulin and the BWE. In contrast, only insulin was effective for stimulation of p70$^{S6K}$ (Thr$^{389}$) phosphorylation. PI3K is required for p70$^{S6K}$ phosphorylation on the Thr$^{389}$ residue but is independent of the Thr$^{421}$ residue. Phosphorylation of ribosomal protein S6, which leads to protein synthesis, is downstream from phosphorylation of both p70$^{S6K}$ residues (Thr$^{421}$ and Thr$^{389}$). Insulin requires activation of the insulin receptor for its downstream effects, whereas the BWE of the present invention has a different entry point. The results of the present study suggest that another component in BWE besides D-CI or MI is responsible for the insulin-mimetic effects.

EXAMPLE 4

The liver plays a central role in glucose metabolism and it is known that a primary effect of insulin administration is the stimulation of glucose uptake in the liver. The objectives of the present study were to determine the effects of the BWE, D-CI, and MI versus insulin on glucose uptake using H4IIE cells.

Tissue culture media, antibiotics, fetal bovine serum (FBS) and Nunc tissue culture plates were purchased from Gibco- BRL (division of Invitrogen Canada Inc.). Insulin (Sigma-Aldrich Canada Ltd.) was dissolved in water and added directly to cells at a final concentration of $10^{-6}$ M. The buckwheat extract was prepared and analyzed as in Example 1. Two µL of the buckwheat extract were added directly to cells unless otherwise indicated. Myo-inositol (Sigma Aldrich Canada Ltd.) and D-chiro-inositol (Industrial Research Ltd.) were dissolved in water at an equal concentration to the amounts present in the BWE (Table 3) and 2 µL of each solution was added directly to cells.

1-butanol was obtained from Sigma-Aldrich Canada Ltd. PD98059 was obtained from New England Biolabs Inc. AG1024 was purchased from EMD Biosciences Inc. Inhibitor details are provided in Table 8-1. $^3$H-deoxyglucose was purchased from New England Nuclear/Perkin Elmer. General laboratory chemicals were purchased from Sigma. Ultrapure chemicals were obtained were obtained from Invitrogen Canada Inc., Bio-Rad Laboratories, and Roche Diagnostics Canada.

Rat H4IIE hepatoma cells (American Type Culture Collection, CRL 1548) were cultured as described in Example 3. Briefly, cells were maintained in α-modified Eagle's media containing 10% FBS, 2 mM glutamine, 50 µg·mL$^{-1}$ streptomycin and 50 µg·mL$^{-1}$ penicillin. Cells were plated and grown to 70% confluence. All cells were placed into serum-free medium for 72 h before addition of stimulating agents to ensure entry into a quiescent state.

$^3$H-deoxyglucose uptake was assayed using the method disclosed by Harrison et al. (1990, J. Biol. Chem. 265(10): 5793-5801). Quiescent H4IIE cells, in 24-well culture dishes containing 1 mL serum-free medium, were washed three times with physiological salt solution (PSS) (5 M NaCl, 2 M KCl, 1 M Hepes, 1 M MgSO$_4$, 0.2 M Na$_2$HPO$_4$, 0.5 M CaCl$_2$, pH 7.4). Cells were placed into 0.5 mL PSS and pre-incubated with inhibitors for 10 minutes prior to the 20 minute stimulation with treatments (insulin, BWE, D-CI, MI). For all experiments, insulin was added at a concentration of $10^{-6}$ M whereas 2 µL volumes of the BWE, D-CI, or MI (0.4% v/v final concentration) were added to cells unless otherwise indicated in figures. Sugar uptake was initiated by the addition of $^3$H-deoxyglucose to a final assay concentration of 0.1 mM glucose (1 mCi/mL) and the cells were subsequently incubated for 5 minutes at 37° C. After two rapid washes with ice-cold PSS (0.5-1 mL/well), the cells were solubilized with 0.4 mL of 0.1% SDS, and $^3$H was detected in 3 mL of EcoL-ume scintillant (MP Biomedicals Inc., Costa Mesa, Calif., USA, 92626).

Statistical significance between treatments was determined by one-way ANOVA and by Duncan's multiple range test for means testing (SAS v.9.1, SAS Institute Inc., Cary, N.C.). Differences were accepted as significant at p<0.05. Data are expressed as the mean±SE.

The data in Example 2 demonstrate that BWE of the present invention lowers serum glucose concentrations in STZ rats. Since insulin has the same effect, we compared the ability of BWE, insulin and two insulin-mimetic compounds (D-CI and MI) to stimulate glucose uptake by H4IIE hepatoma cells. Quiescent H4IIE cells were placed into glucose-free medium and stimulated with these agents for 10 minutes. Radio-labelled deoxyglucose was added to the medium and glucose uptake was determined by the detection of $^3$H in cells.

Figure 20:
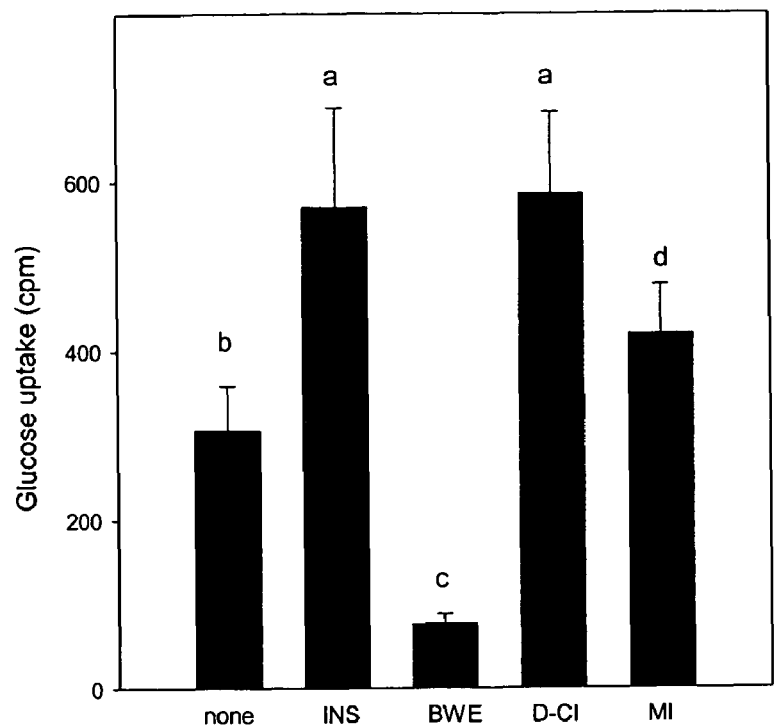
FIG. 20 shows the effects of insulin (INS), BWE, D-chiro-inositol (D-CI) and myo-inositol (MI) on the uptake of $^3$H-deoxy-glucose by H4IIE cells.
Figure 21:
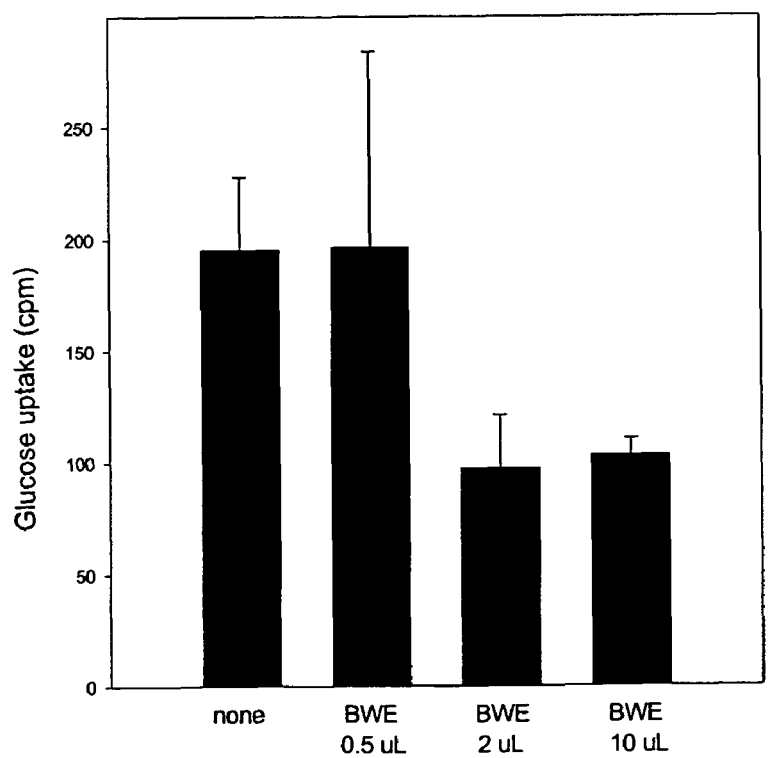
FIG. 21 shows the dose-dependent effects of BWE on inhibition of $^3$H-deoxy-glucose uptake in H4IIE cells. The data are presented as means±SE for three independent experiments.
Figure 22:
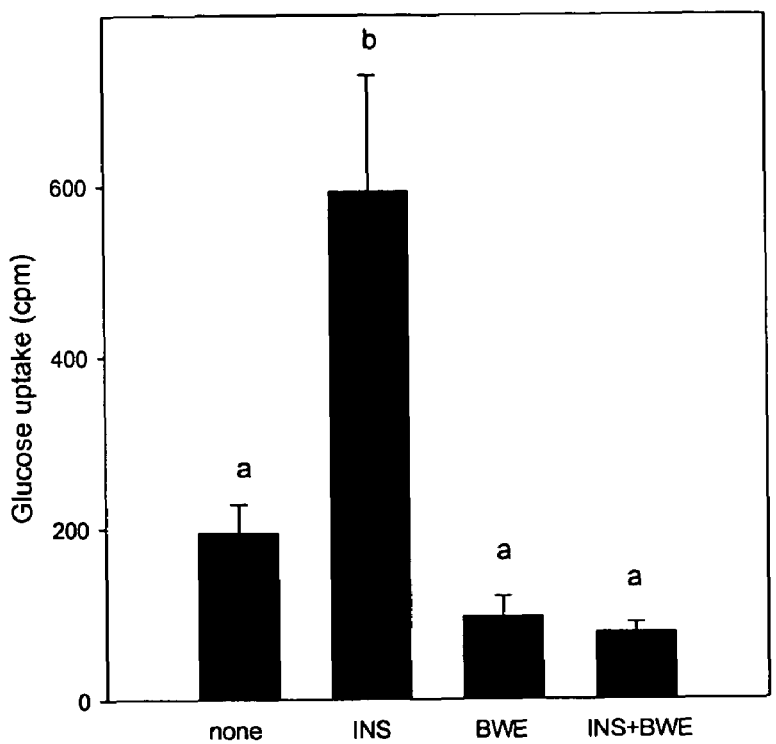
FIG. 22 shows the effects of BWE and insulin (INS) on basal $^3$H-deoxy-glucose uptake in H4IIE cells. The effects of BWE on INS-stimulated (I+B) glucose uptake were also determined. The data are presented as means±SE for three independent experiments. Statistical significance ($p<0.05$) was determined by ANOVA and Duncan's multiple range test and bars with different letters are significantly different.
Figure 23:
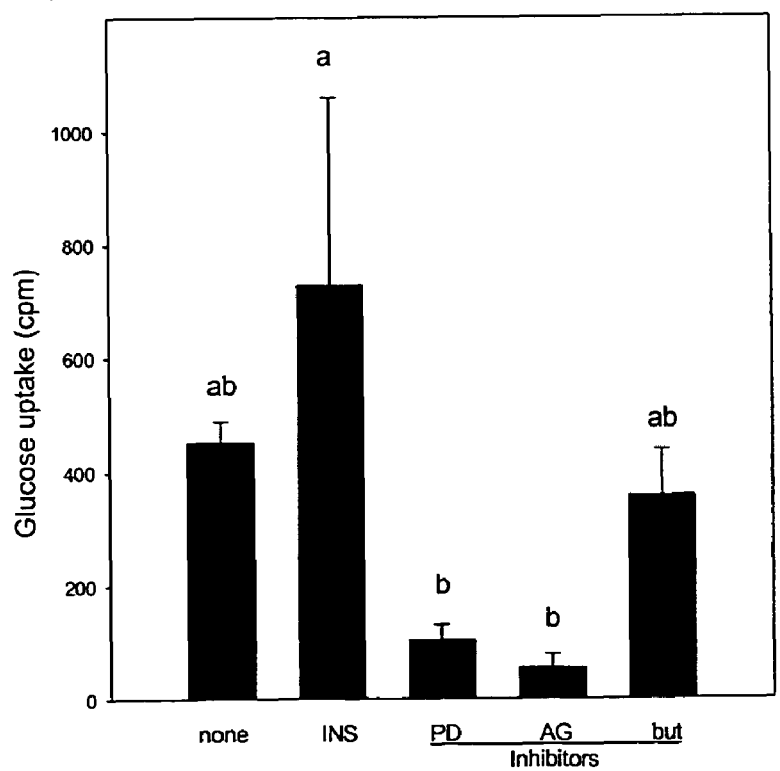
FIG. 23 shows the effects of inhibiting the phosphorylation of MAPK by PD98059 (PD), insulin receptor tyrosine kinase by AG1024 (AG) and phospholipase D by butanol (but) on insulin (INS)-stimulated $^3$H-deoxy-glucose uptake in H4IIE cells. The data are presented as means±SE for three independent experiments. Statistical significance ($p<0.05$) was determined by ANOVA and Duncan's multiple range test and bars with different letters are significantly different.

As shown in FIG. 20, the insulin and D-CI treatments stimulated glucose uptake. While MI also appeared to increase glucose uptake, the effects were not statistically different from untreated cells. In contrast, BWE did not stimulate glucose uptake, but rather, significantly inhibited basal glucose uptake (FIG. 20). We investigated the dose-dependent effects of BWE on the inhibition of basal glucose uptake and found that 0.5 µL of the BWE (0.1% v/v final concentration) did not affect basal glucose uptake whereas 2 µL and 10 µL of the BWE (0.4% and 2%, respectively) decreased the basal rate of glucose uptake (FIG. 21). Furthermore, adding the BWE to cells 10 minutes prior to treatment with insulin resulted in inhibition of glucose uptake (FIG. 22). We also investigated the contribution of various signal transduction mediators on insulin-stimulated glucose uptake. Inhibition of the phosphorylation of MAPK (PD98059 sensitive) and insulin receptor tyrosine kinase (AG420 sensitive) decreased insulin-stimulated glucose uptake (FIG. 23). Thus, activation of these proteins is required for insulin to stimulate glucose uptake. Inhibiting phospholipase D (butanol sensitive) also decreased insulin-stimulated glucose uptake although the effect was not significant (FIG. 23).

The increase in glucose uptake by H4IIE hepatoma cells represents an increase in glucose utilization rather than a change in glucose transporter activity since insulin-stimulated glucose uptake in the liver is due to increased metabolic activity. The main finding of this study was that the BWE inhibited glucose uptake in H4IIE cells whereas D-CI and MI stimulated glucose uptake rates similar to those in response to insulin treatments. These results indicate that the presence of D-CI and MI in BWE are not responsible for BWE's antihyperglycemic effects.

EXAMPLE 5

It is known that buckwheat seeds contain significant quantities of flavonoid compounds including quercetin glucosides such as rutin (Oomah et al., 1996, J. of Agric. Food Chem. 44: 1746-1750; Fabjan et al., 2003, J. of Agric. Food Chem. 51:6452-6455). Published U.S. Patent Application No. 2006/002969 disclosed that flavonoids extracted from buckwheat with ethanol were useful for treatment of hyperglycemia. It also appears that multiple low doses of rutin may slow or prevent the onset of hyperglycemia (Srinivasan et al., 2005, Indian J. Pharmacol. 37: 327-328). The objectives of the present study were to assess and compare the effects on H4IIE cells of BWE, rutin extracted from BWE, and a commercial rutin source versus insulin on MAP kinase enzyme activity and on glucose uptake.

Tissue culture media, antibiotics, fetal bovine serum (FBS) and Nunc tissue culture plates were purchased from Invitrogen Canada Inc. (Burlington, Ontario, Canada, L7P 1A1). Insulin (Sigma-Aldrich Canada Ltd., Oakville, Ontario, Canada, L6H 6J8) was dissolved in water and added directly to cells at a concentration of 250 nM unless otherwise indicated. Rutin trihydrate produced by Fluka BioChemika, was obtained from Sigma-Aldrich Canada Ltd.

Buckwheat variety Koto (*Fagopyrum esculentum*, Moench) de-hulled seeds obtained from Kade Research Ltd. (Morden, Manitoba, Canada) were ground into a fine powder with a standard coffee grinder. Ten-gram samples of the ground buckwheat were placed into separate air-dry Soxhlet extraction thimbles (Sigma-Aldrich Canada Ltd.) after which, each sample-containing thimble was placed into an extraction chamber which was then interposed: (a) a round-bottomed receiving flask provided with several boiling chips and 100 ml of a selected extraction solvent, and (b) a condenser unit for recovering and returning solvent vapours to the receiving flask. The open end of the condenser unit was plugged with cotton to prevent sample loss during the extraction procedure. The solvent was then heated to its boiling point and allowed to reflux for 1 hour after which, the receiving flask was separated from the extraction chamber and the solvent was removed via rotary evaporation thereby producing a dried BWE. The dried solvent-extracted BWE samples were transferred to storage bottles, labelled and sealed until required for subsequent analyses and assessments described below. Individual samples of ground buckwheat seeds were extracted with one of ethanol, methanol, acetone and acetonitrile.

Sepaharose LH-20 (Amersham Biosciences) was allowed to swell overnight in water, then poured into a column and equilibrated with water. A dried BWE sample was suspended in water, then applied to the column. The column was washed with 10 column volumes of water, followed by serially elution with 10-column volumes of a selected solvent. The following solvents were used: acetone, ethanol, methanol (MeOH), ether, acetonitrile ($CH_3CN$), dichloromethane ($CH_2Cl_2$), tetrahydrafuran (THF), water, hexane, and chloroform ($CHCl_3$).

The presence of rutin in the eluants from the solvent extractions was detected by HPLC. A C18 column (Sigma-Aldrich Canada Ltd.) was equilibrated with 5% acetonitrile for 10 min before each run. Dried samples were suspended in water prior to injection: The column was subsequently eluted with a gradient going from 5% to 100% acetonitrile over a 60-min time period. The column was maintained in 100% acetonitrile for 10 min, after which the acetonitrile was reduced to 5% over 10 min. The eluate was monitored by absorbance at 280 nm.

Rat H4IIE hepatoma cells (American Type Culture Collection, CRL 1548) were cultured as described in Example 3. Briefly, cells were maintained in α-modified Eagle's media containing 10% FBS, 2 mM glutamine, 50 µg·mL$^{-1}$ streptomycin and 50 µg·mL$^{-1}$ penicillin. Cells were plated and grown to 70% confluence. All cells were placed into serum-free medium for 72 h before addition of stimulating agents to ensure entry into a quiescent state. Quiescent H4IIE cells, in 24-well culture dishes containing 1 mL serum-free medium, were washed three times with physiological salt solution (PSS) (5 M NaCl, 2 M KCl, 1 M Hepes, 1 M $MgSO_4$, 0.2 M $Na_2HPO_4$, 0.5 M $CaCl_2$, pH 7.4).

Fractions (~1.0 ml) from each solvent extraction were collected and assayed for their effects on MAPK activation as described in Example 3. The effects of selected fractions, alone or in combination with insulin, on the uptake of labelled glucose were assessed following the methods described in Example 4. For all experiments, insulin was added at a concentration of 10$^{-6}$ M while BWE treatments were 2-µL volumes (0.4% v/v equivalent of D-CI). The effects of the solvent fractions on H4IIE cells were assessed with 20-min exposure periods after which, sugar uptake was initiated by the addition of $^3$H-deoxyglucose to a final assay concentration of 0.1 mM glucose (1 mCi/mL) and the cells were subsequently incubated for 5 minutes at 37° C. After two rapid washes with ice-cold PSS (0.5-1 mL/well), the cells were solubilized with 0.4 mL of 0.1% SDS, and $^3$H was detected in 3 mL of EcoLume scintillant.

Figure 24:
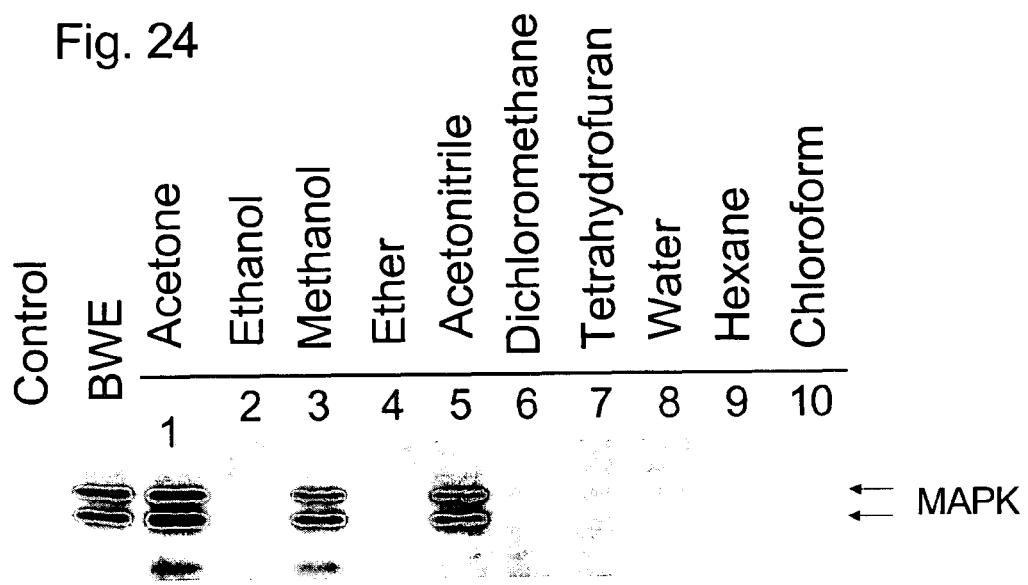
FIG. 24 shows the effects of crude BWE, and purified fractions extracted with non-polar solvents, polar aprotic solvents, and polar protic solvents on phosphorylation of MAP kinase activity, assessed by Western blot analysis. H4IIE cells were treated with each agent individually for 6 minutes, with untreated cells serving as the control (CTRL)
Figure 25:
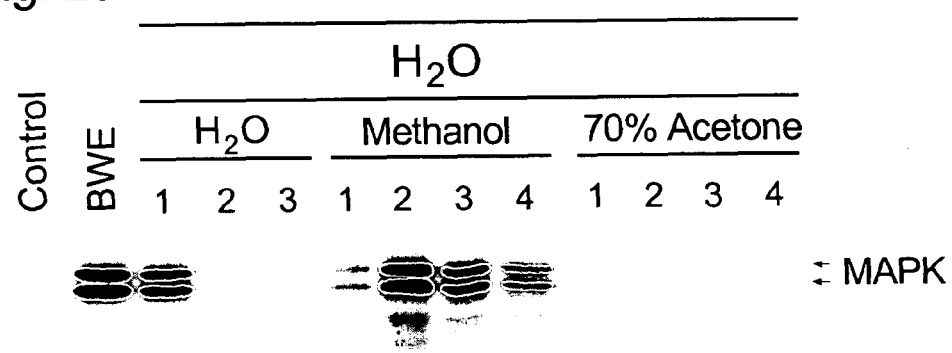
FIG. 25 shows the effects of crude BWE, and sequential fractions eluted from the crude BWE with multiple solvents on phosphorylation of MAP kinase activity, assessed by Western blot analysis. H4IIE cells were treated with each agent individually for 6 minutes, with untreated cells serving as the control (CTRL)
Figure 26:
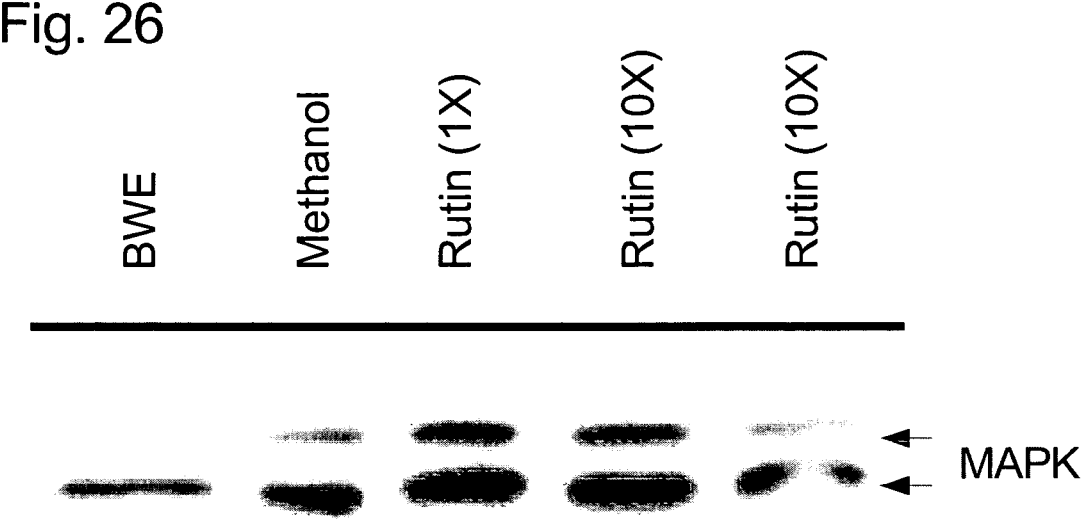
FIG. 26 compares the effects of crude BWE and a purified fraction from the crude BWE with increasing concentrations of synthetic rutin on phosphorylation of MAP kinase activity, assessed by Western blot analysis. H4IIE cells were treated with each agent individually for 6 minutes, with untreated cells serving as the control (CTRL)

The data in FIG. 24 show that MAPK enzyme activity was stimulated by a crude BWE of the present invention as well as by components extracted from buckwheat with acetone, methanol and acetonitrile. The data in FIG. 25 demonstrate that the MAPK-stimulating activity of BWE can be purified by column chromatography on Sepharose LH-20 after serial elution with water, methanol and acetone. Although the first water fraction containing flowthrough material exhibited MAKP stimulating activity, the bulk of the activity was recovered upon elution with methanol. No activity remained on the column as indicated by the lack of activity in fractions obtained during acetone elution. The data in FIG. 26 compare the effects on MAPK activity of the H4IIE hepatic cells by 6-min incubations with one of the crude BWE, a methanol extract from buckwheat, and 0.011 mM rutin (1×), 0.11 mM rutin (10×), and 5.6 mM rutin (50×). Each of the treatments stimulated MAKP enzyme activity. In summary, the Western blot data shown in FIGS. 24, 25 and 26 provide evidence that the BWE extract of the present invention contains a component that stimulates MAPK activity and suggest that the flavenoid rutin is the causative compound.

Figure 27:
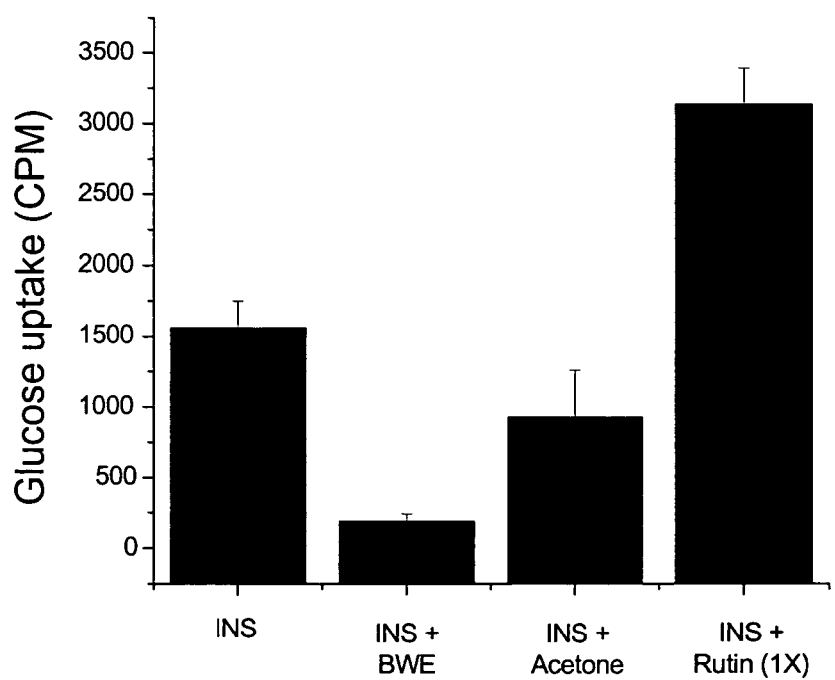
FIG. 27 compares the effects of insulin with insulin amended with one of crude BWE, a purified BWE component, and rutin, on the uptake of $^3$H-deoxy-glucose by H4IIE cells.

FIG. 27 shows the effects of insulin, synthetic rutin, the crude BWE, and an MAPK-stimulating component from buckwheat. The data clearly indicate combining insulin with the BWE significantly reduces glucose uptake by hepatoma cells while combining insulin with 0.011 mM rutin significantly stimulated glucose uptake. Furthermore, the combination of insulin and a MAPK-stimulating component from buckwheat did not have a significant effect on glucose uptake. Therefore, these data indicate that rutin-like flavonoid components present in the BWE extract are not the causative compounds for inhibition of glucose uptake by hepatic cells.

EXAMPLE 6

The data presented in the previous examples clearly show that the BWE of the present invention comprises a glucose-uptake inhibiting component that is exclusive of MI, D-CI, and rutin-like flavonoids. It is evident that this novel component is soluble in: (1) polar aprotic solvents such as tetrahydofuran, acetone, and acetonitrile, and also in (2) polar protic solvents such as ethanol, methanol and water. The objectives of the present study were to determine the glucose-uptake inhibiting BWE component is soluble in non-polar solvents and to further purify the component.

Buckwheat variety Koto (Fagopyrum esculentum, Moench) de-hulled seeds obtained from Kade Research Ltd. (Morden, Manitoba, Canada) were ground into a fine powder with a standard coffee grinder. Ten-gram samples of the ground buckwheat were placed into separate air-dry Soxhlet extraction thimbles (Sigma-Aldrich Canada Ltd.) after which, each sample-containing thimble was placed into an extraction chamber which was then interposed: (a) a round-bottomed receiving flask provided with several boiling chips and 100 ml of chloroform, and (b) a condenser unit for recovering and returning solvent vapours to the receiving flask. The open end of the condenser unit was plugged with cotton to prevent sample loss during the extraction procedure. The receiving flask containing the chloroform was heated to about 62° C. and then allowed to reflux for 45-60 min after which, the chloroform-containing receiving flask was removed from the extraction chamber and replaced with a second flask containing 100 ml of tetrahydrofuran. The tetrahydrofuran containing flask was heated to about 66° C. and then allowed to reflux for 45-60 min after which, the tetrahydrofuran-containing receiving flask was removed from the extraction chamber and replaced with a third flask containing 100 ml of acetone, or alternatively 100 ml of methanol. The third flask was heated to about 56° C. if it contained acetone (or to about 65° C. if it contained methanol) and allowed to reflux for 45-60 min after which the sample-containing solvent was removed by rotary evaporation. It was determined that methanol was the most suitable solvent for re-suspending the purified dried extract.

Figure 28:
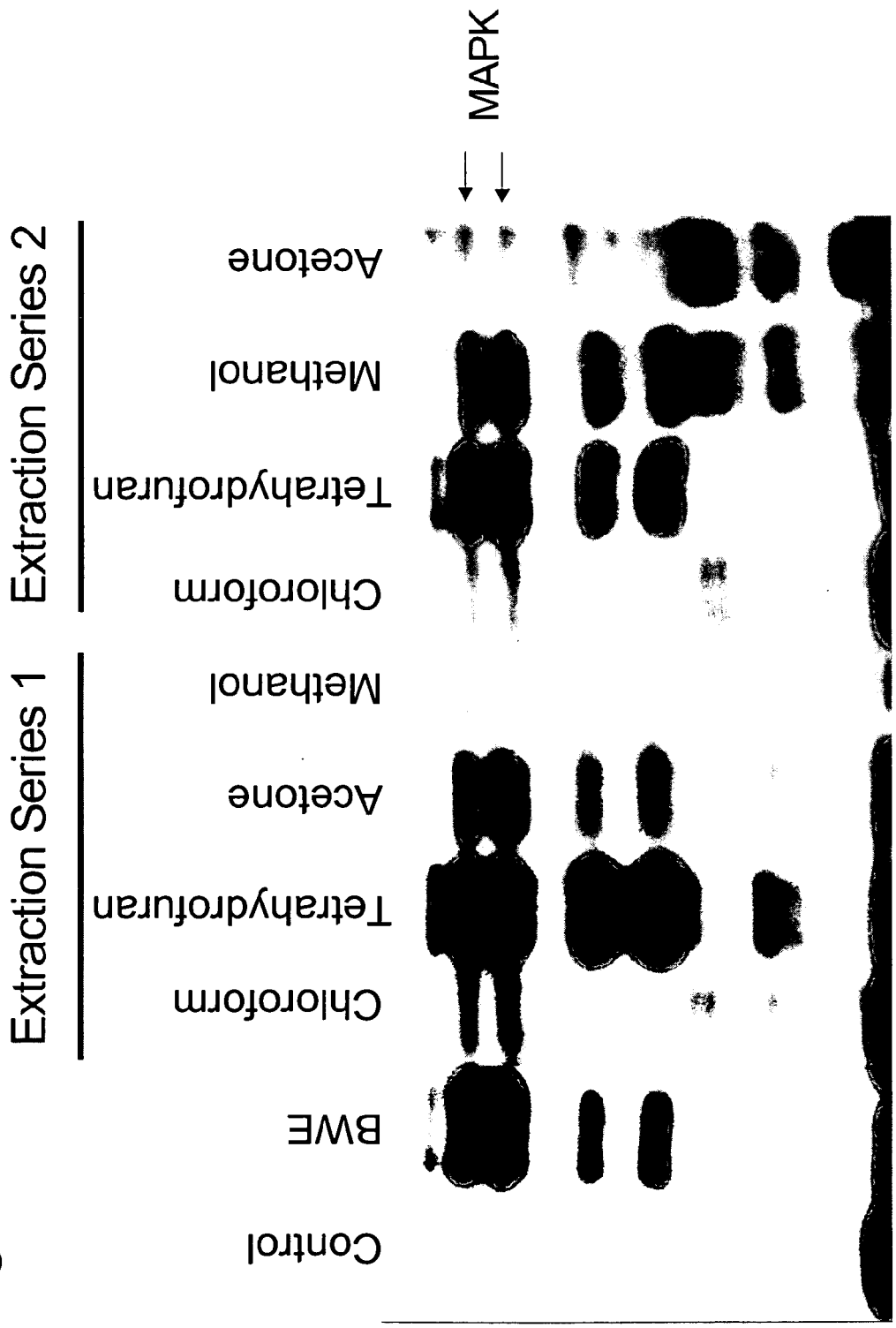
FIG. 28 compares the effects of purified fractions from BWE with crude BWE on phosphorylation of MAP kinase activity in H4IIE hepatoma cells, assessed by Western blot analysis. H4IIE cells were treated with each agent individually for 6 minutes, with untreated cells serving as the control (CTRL)

The effects of the purified extracts on MAPK activity were monitored by administering 10-µl aliquots to separate groups of quiescent H4IIE cells as described previously. The cells were harvested with 2× sample buffer after a 10-min incubation and phosphorylation of MAP kinase was monitored by Western blot analysis. The data collected were compared to data from control H4IIE cells that did not receive any treatments, and to H4IIE cells which were treated with the crude BWE. The data in FIG. 28 show that the MAPK activity is solubilised by polar aprotic solvents (i.e., tetrahydrofuran, acetone) and a polar protic solvent (i.e., methanol).

Figure 29:
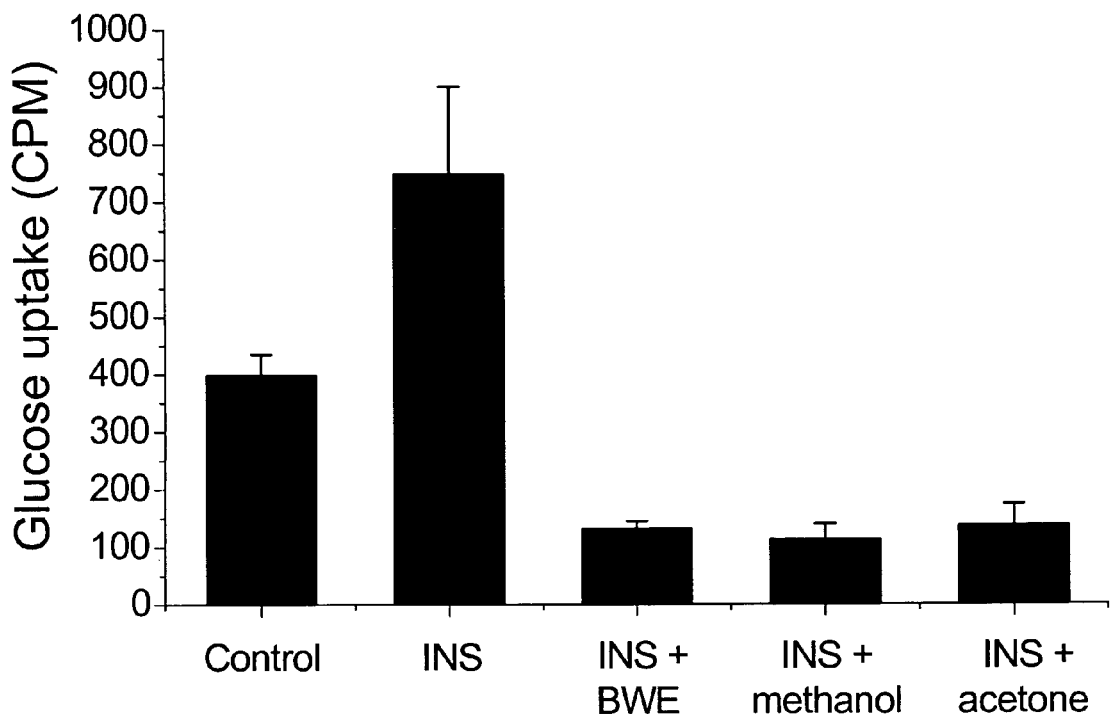
FIG. 29 compares the effects of insulin with insulin amended with one of crude BWE and BWE components purified with a novel multi-step process, on the uptake of $^3$H-deoxy-glucose by H4IIE cells.

The effects of the purified extracts on inhibition of glucose uptake were assessed with the glucose uptake assay conducted with H4IIE cells as described previously. In this study, the H4IIE cells received a 20-min exposure to one of the following treatments; insulin, insulin plus crude BWE, insulin plus an aliquot of an acetone extract from the third step of the purification process (extraction series 1), and insulin plus an aliquot of a methanol extract from the third step of the purification process (extraction series 2). All treatments then received a 5-min exposure at 37° C. to $^3$H-deoxyglucose (final assay concentration of 0.1 mM glucose (1 mCi/mL)). After two rapid washes with ice-cold PSS (0.5-1 mL/well), the cells were solubilized with 0.4 mL of 0.1% SDS, and $^3$H was detected in 3 mL of EcoLume scintillant. The data in FIG. 29 show that insulin stimulated glucose uptake by H4IIE cells while cells receiving insulin treatments amended with the crude BWE or an extract purified by the three-step process disclosed herein, significantly inhibited glucose uptake.

While particular exemplary embodiments of the present invention have been described in the foregoing, it is to be understood that other embodiments are possible within the scope of the present invention and are intended to be included herein. In view of numerous changes and variations that will be apparent to persons skilled in the art, the scope of the present invention is to be considered limited solely by the appended claims.

The invention claimed is:

1. A method for providing an extract from buckwheat seed wherein the extract is effective for inhibiting systemic glucose uptake into an individual's blood stream, said method comprising:
    contacting buckwheat seed with a first solvent to produce a first extract, said first solvent comprising a non-polar solvent;
    contacting said buckwheat seed a second time with a second solvent to produce a second extract, said second solvent comprising a polar aprotic solvent;
    contacting said buckwheat seed a third time with a third solvent to produce a third extract, said third solvent selected from the group comprising polar aprotic solvents and polar protic solvents; and
    drying said third extract to remove the third solvent therefrom.

2. The method according to claim 1 wherein the first solvent is a non-polar solvent selected from the group consisting of hexane, benzene, toluene, diethyl ether, chloroform, ethyl acetate, and dichloromethane.

3. The method according to claim 2 wherein the first solvent is chloroform.

4. The method according to claim 1 wherein the second solvent is a polar aprotic solvent selected from the group consisting of 1,4-dioxane, tetrahydrofuran, acetone, acetonitrile, dimethylformamide, and dimethyl sulfoxide.

5. The method according to claim 4 wherein the second solvent is tetrahydrofuran.

6. The method according to claim 1 wherein the third solvent is a polar aprotic solvent selected from the group consisting of 1,4-dioxane, tetrahydrofuran, acetone, acetonitrile, dimethylformamide, and dimethyl sulfoxide.

7. The method according to claim 6 wherein the third solvent is a polar aprotic solvent selected from the group consisting of acetone and acetonitrile.

8. The method according to claim 1 wherein the third solvent is a polar protic solvent selected from a group consisting of acetic acid, n-butanol, isopropanol, n-propanol, ethanol, methanol, formic acid, and water.

9. The method according to claim 8 wherein the third solvent is a polar protic solvent selected from the group comprising.

10. The method according to claim 1 wherein the first solvent is chloroform, the second solvent is tetrahydrofuran, and the third solvent is selected from the group consisting of acetone and methanol.

11. The method according to claim 1 wherein the buckwheat seed comprises dehulled buckwheat seed.

12. The method according to claim 10 wherein the dehulled buckwheat seed comprises buckwheat groats.

13. The method according to claim 12 wherein the buckwheat groats are powdered.

14. A dried extract from buckwheat seed produced according to claim 1.

15. The dried extract of claim 14 wherein the extract comprises at least one naturally occurring compound effective for inhibiting systemic glucose uptake into an individual's blood stream.

16. The dried extract of claim 14 wherein the extract comprises at least one naturally occurring compound effective for inhibiting a sodium-dependent glucose transporter.

17. A nutraceutical composition for use in managing serum glucose levels in a diabetic individual, said composition comprising;
    the dried extract according to claim 14; and
    a nutraceutical carrier.

18. A functional food composition for use in managing serum glucose levels in a diabetic individual, said composition comprising:
    the dried extract according to claim 14; and
    a functional food carrier.

19. The functional food composition according to claim 18 wherein the functional food carrier is selected from the group comprising powders, liquids, gels, and pastes.

20. A method for managing serum glucose levels in a diabetic individual, said method comprising administering to the individual a nutraceutical composition according to claim 17 in an effective amount.

21. A method for managing serum glucose levels in a diabetic individual, said method comprising administering to the individual a functional food composition according to claim 18 in an effective amount.

* * * * *